US008026049B2

(12) United States Patent
Assadi-Porter et al.

(10) Patent No.: US 8,026,049 B2
(45) Date of Patent: Sep. 27, 2011

(54) NONINVASIVE MEASUREMENT AND IDENTIFICATION OF BIOMARKERS IN DISEASE STATE

(75) Inventors: Fariba Masoumeh Assadi-Porter, Fitchburg, WI (US); Mark E. Cook, Madison, WI (US); Hamid Reza Eghbalnia, Madison, WI (US); Marco Tonelli, Madison, WI (US); Warren Paul Porter, Fitchburg, WI (US); Daniel Elmer Butz, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 624 days.

(21) Appl. No.: 12/054,153

(22) Filed: Mar. 24, 2008

(65) Prior Publication Data

US 2009/0104596 A1     Apr. 23, 2009

Related U.S. Application Data

(60) Provisional application No. 60/896,645, filed on Mar. 23, 2007.

(51) Int. Cl.
*C12Q 1/70* (2006.01)
*G01N 33/00* (2006.01)
*G01N 33/53* (2006.01)

(52) U.S. Cl. ................................ 435/5; 435/4; 435/7.92

(58) Field of Classification Search ........................ None
See application file for complete search history.

(56) References Cited

U.S. PATENT DOCUMENTS

| | | | |
|---|---|---|---|
| 5,912,178 | A | 6/1999 | Porter et al. |
| 7,465,276 | B2 | 12/2008 | Assadi-Porter et al. |
| 2006/0241869 | A1 | 10/2006 | Schadt et al. |

OTHER PUBLICATIONS

Abbott et al. (2005) "Androgen Excess Fetal Programming of Female Reproduction: A Developmental Aetiology for Polycystic Ovary Syndrome," *Hum. Reprod. Update* 11(4):357-374.
Anderson et al (Nov. 7, 2003) "Deaths: Leading Causes for 2001," *Nat. Vital Stat. Rep.* 53:1-85.
Andersson et al. (2004) "Data Preprocessing by Wavelets and Genetic Algorithms for Enhanced Multivariate Analysis of LC Peptide Mapping," *J. Pharm. Biomed. Anal.* 34(3):531-541.
Antoniotti et al. (2003) "Model Building and Model Checking for Biochemical Processes," *Cell. Biochem. Biophys.* 38(3):271-286.
Aranibaar et al. (2006) "Metabolomic Analysis Using Optimized NMR and Statistical Methods," *Anal. Biochem.* 355(1):62-70.
Birkemeyer et al. (Jan. 2005) "Metabolome Analysis: The Potential of in Vivo Labeling with Stable Isotopes for Metabolite Profiling," *Trends Biotechnol.* 23(1):28-33.
Butz et al. (Nov. 2006) "t10, c12 Conjugated Linoleic Acid Induces Compensatory Growth After Immune Challenge," *J. Nutr. Biochem.* 17(11):735-741.
Bylund et al. (2002) "Chromatographic Alignment by Warping and Dynamic Programming as a Pre-Processing Tool for PARAFAC Modeling of Liquid Chromatography-Mass Spectrometry Data," *J. Chromatogr. A.* 961(2):237-244.
Clote et al. (2006) "Symmetric Time Warping, Boltzmann Pair Probabilities and Functional Genomics," *J. Math. Biol.* 53(1):135-161.
Crampin et al. (2004) "Mathematical and Computational Techniques to Deduce Complex Biochemical Reaction Mechanisms," *Prog. Biophys. Mol. Biol.* 86(1):77-112.
Diamanti-Kandarakis et al. (Feb. 23, 2006) "Indices of Low-Grade Chronic Inflammation in Polysystic Ovary Syndrome and the Beneficial Effect of Metformin," *Hum. Reprod.* 21(6):1426-1431.
Diamanti-Kandarakis et al. (2006) "Inflammatory and Endothelial Markers in Women with Polycystic Ovary Syndrome," *Eur. J. Clin. Invest.* 36(10):691-697.
Dumas et al. (Apr. 1, 2006) "Assessment of Analytical Reproducibility of 1H NMR Spectroscopy Based Metabonomics for Large-Scale Epidemiological Research: The INTERMAP Study," *Anal. Chem.* 78(7):2199-2208.
Eghbalnia et al. (2005) "High-Resolution Iterative Frequency Identification for NMR as a General Strategy for Multidimensional Data Collection," *J. Am. Chem. Soc.* 127(36):12528-12536.
Eghbalnia et al. (2005) "Probabilistic Identification of Spin Systems and their Assignments Including Coil-Helix Inference as Output (PISTACHIO)," *J. Biomol. NMR* 32(3):219-233.
Eghbalnia et al. (2005) "Protein Energetic Conformational Analysis from NMR Chemical Shifts (PECAN) and its Use in Determining Secondary Structural Elements," *J. Biomol. NMR* 32(1):71-81.
Ferraz et al. (2004) "Comparison of Six Methods for the Extraction of Lipids from Serum in Terms of Effectiveness and Protein Preservation," *J. Biochem. Biophys. Meth.* 58(3):187-193.
Fiehn, O. (2002) "Metabolomics—The Link Between Genotypes and Phenotypes," *Plant. Mol. Biol.* 48(1-2):155-171.
Finley et al. (Mar. 14, 2006) "Commentary: Where and How could Biomarkers be used in 2016," *Aaps J.* 8(1):E185-E189.
Fleming et al. (2006) "The Use of Insulin Sensitizing Agents in Ovulation Induction in Women with Polycystic Ovary Syndrome," *Hormones* 5(3):171-178.
Forshed et al. (2005) "A Comparison of Methods for Alignment of NMR Peaks in the Context of Cluster Analysis," *J. Pharm. Biomed. Anal.* 38(5):824-832.
Franke et al. (Jun. 2006) "Reconstruction of a Functional Human Gene Network, with an Application for Prioritizing Positional Candidate Genes," *Am. J. Hum. Genet.* 78(6):1011-1025.

(Continued)

*Primary Examiner* — Robert A Zeman
(74) *Attorney, Agent, or Firm* — Greenlee Sullivan P.C.

(57) ABSTRACT

The invention is methods and related kits for diagnosing a disease state of cachexia by measuring biomarker profiles from a biological sample. Rapid measurement of early onset or progression of the disease in a subject is determined by measuring biomarker levels from the subject and optionally comparing the biomarker levels to a standard biomarker profile or metabolome phase portrait for the disease. The biomarkers measured in the assay and related kit for cachexia progression include biomarkers selected from the group consisting of lactate, citrate, formate, acetoacetate, 3-hydroxy butrate, alanine, glutamine, glutamate, valine, isoleucine leucine, thrionine, lysine, arginine, tyrosine, phenyl alanine, histidine and tryptophan.

9 Claims, 35 Drawing Sheets

OTHER PUBLICATIONS

Hatch et al. (Jul. 16, 1995) "Early Detection of Catabolic State via Change in 13C/12C Ratios of Blood Proteins," *BBRC* 212(3):719-726.

Hollywood et al. (2006) "Metabolomics: Current Technologies and Future Trends," *Proteomics* 6(17):4716-4723.

Hotamisligil et al. (Jan. 1, 1993) "Adipose Expression of Tumor Necrosis Factor-Alpha: Direct Role in Obesity-Linked Insulin Resistance," *Science* 259(5091):87-91.

Hu et al. (Web Release Feb. 16, 2006) "Time-Dependant Sensitivity Analysis of Biological Networks: Coupled MAPK and PI3K Signal Transduction Pathways," *J. Phys. Chem. A Mol. Spectrosc. Kinet. Environ. Gen Theory* 110(16):5361-5370.

Kano et al. (1992) "Increased Alpha-Hydroxybutyrate Dehydrogenase in Serum from Children with Measles," *Clin. Chem.* 38(5):624-627.

Klasing et al. (1984) "Changes in Protein Synthesis Due to an Inflammatory Challenge," *Proc. Soc. Exp. Biol. Med.* 176:285-291.

Krabbe et al. (Mar. 2001) "Ageing is Associated with a Prolonged Fever Response in Human Endotoxemia," *Clin. Diag. Lab. Immun.* 8(2):333-338.

Krishnan et al. (Jan. 2005) "Metabolite Fingerprinting and Profiling in Plants Using NMR," *J. Exp. Bot.* 56(410):255-265.

Kummel et al. (2006) "Putative Regulatory Sites Unraveled by Network-Embedded Thermodynamic Analysis of Metabolome Data," *Mol. Syst. Biol.* 2: 2006-0034.

Legro et al. (1999) "Prevalence and Predictors of Risk for AType 2 Diabetes Mellitus and Impaired Glucose Tolerance in Polycycstic Ovary Syndrome: A Prospective Controlled Study in 254 Affected Women," *J. Clin. Endocrinol. Metab.* 84(1):165-169.

Li et al. (Web Release Feb. 6, 2004) "Inferring Pathways and Networks with a Bayesian Framework," *FASEB J.* 18(6):746-748.

Mendes et al. (2005) "Modeling and Simulation for Metabolomics Data Analysis," *Biochem. Soc. Trans.* 33(6):1427-1429.

Nicholson, J.K. (Oct. 3, 2006) "Global Systems Biology, Personalized Medicine and Molecular Epidemiology," *Mol. Syst. Biol.* 2:52-57.

Pickup et al. (1998) "Is Type II Diabetes Mellitus a Disease of the Innate Immune System," *Diabetologia* 41(10):1241-1248.

Pillay et al. (Dec. 16, 2006) "The Association Between Polycystic Ovaries and Endometrial Cancer," *Hum. Reprod.* 21(4):924-929.

Prakash et al. (2006) "Signal Maps for Mass Spectrometry-Based Comparative Proteomics," *Mol. Cel. Proteomics* 5(3):423-432.

Price et al. (Oct. 2004) "Uniform Sampling of Steady-State Flux Spaces: Means to Design Experiments and to Interpret Enzymopathies," *Biophys. J.* 87(4):2172-2186.

Prince et al. (Sep. 1, 2006) "Chromatographic Alignment of ESI-LC-MS Proteomics Data Sets by Ordered Bijective Interpolated Warping," *Anal. Chem.* 78(17):6140-6152.

Purohit et al. (2004) "Discrimination Modes Using Variance-Stabilizing Transformation of Metabolomic NMR Data," *Omics* 8(2):118-130.

Rewers et al. (2006) "Bedside Monitoring of Blood β-Hydroxybutyrate Levels in the Management of Diabetic Ketoacidosis in Children," *Diab. Technol. Ther.* 8(6):671-676.

Rochfort, S. (Web Release Nov. 9, 2005) "Metabolomics Reviewed: A New 'Omics' Platform Technology for Systems Biology and Implications for Natural Products Research," *J. Nat. Prod.* 68(12):1813-1820.

Romano et al. (2002) "A New Time-Domain Frequency-Selective Quantification Algorithm," *J. Magn. Res.* 155(2):226-235.

Romano et al. (2000) "A Time-Domain Algorithm for NMR Spectral Normalization," *J. Magn. Reson.* 146(1):89-99.

Romano et al. (1999) "A New Algorithm for NMR Spectral Normalizations," *J. Magn. Reson.* 138(1):115-122.

Schadt et al. (2006) "Thermatic Review Series: Systems Biology Approaches to Metabolic and Cardiovascular Disorders. Reverse Engineering Gene Networks to Identify Key Drivers of Complex Disease Phenotypes," *J. Lipid Res.* 47(12):2601-2613.

Sharma et al. (1992) "Kinetics of Endotoxin-Induced Acute-Phase Protein Gene Expression and Its Modulation by TNF-Alpha Monoclonal Antibody," *Am. J. Physiol. Reg. Integr. Comp. Physiol.* 262(5):R786-793.

Shortreed et al. (Sep. 15, 2006) "Ionizable Isotopic Labeling Reagent for Relative Quantification of Amine Metabolites by Mass Spectrometry," *Anal. Chem.* 78(18):6398-6403.

Sjøholm et al. (Web Release Jul. 1, 2005) "Inflammation and the Etiology of type 2 Diabetes," *Diab. Metab. Res. Rev.* 22(1):4-10.

Spraul et al. (1994) "Automatic Reduction of NMR Spectroscopic Data for Statistical and Pattern Recognition Classification of Samples," *J. Pharm. Biomed. Anal.* 12(10):1215-1225.

Stoyanova et al. (2002) "NMR Spectral Quantitation by Principal Component Analysis. III. A Generalized Procedure for Determination of Lineshape Variations," *J. Mag. Reson.* 154(2)163-175.

Stoyanova et al. (2004) "Automatic Alignment of Individual Peaks in Large High-Resolution Spectral Data Sets," *J. Magn. Reson.* 170(2):329-335.

Sumner et al. (2003) "Plant Metabolomics: Large-Scale Phytochemistry in the Functional Genomics era," *Phytochemistry* 62(6):817-836.

The Rotterdam, E.A.-s.P.c.w.g (2004) "Revised 2003 Consensus on Diagnostic Criteria and Long-Term Health Risks Related to Polycyctic Ovary Syndrome (PCOS)," *Hum. Reprod.* 19(1):41-47.

van Nederkassel et al. (2006) "A Comparison of Three Algorithms for Chromatograms Alignment," *J. Chromatogr A.* 1118(2):199-210.

Voit et al. (Jun. 20, 2006) "The Intricate Side of Systems Biology," *Proc. Nat. Acad. Sci. USA* 103(25):9452-9457.

Waters et al. (Web Release Mar. 24, 2005) "Metabonomic Deconvolution of Embedded Toxicity: Application to Thioacetamide Hepato-and Nephrotoxicity," *Chem. Res. Toxicol.* 18:639-654.

Webb-Robertson et al. (Web Release Jun. 28, 2005) "A Study of Spectral Integration and Normalization in NMR-Based Metabonomic Analyses," *J. Pharm. Biomed. Anal.* 39(3-4):830-836.

Weckwerth et al. (2002) "Can we Discover Novel Pathways Using Metabolomic Analysis," *Curr. Opin. Biotechnol.* 13(2):156-160.

Weljie et al. (Web Release May 17, 2006) "Targeted Profiling: Quantitative Analysis of 1H NMR Metabolomics Data," *Anal. Chem.* 78(13):4430-4442.

Wu et al. (Web Release Jan. 24, 2006) "Peak Alignment of Urine NMR Spectra Using Fuzzy Warping," *J. Chem. Inf. Model.* 46(2):863-875.

Xu et al. (Dec. 2003) "Chronic Inflammation in Fat Plays a Crucial Role in the Development of Obesity-Related Insulin Resistance," *J. Clin Invest.* 112(12):1821-1830.

Yang et al. (2000) "Dietary Conjugated Linoleic Acid Protects Against end Stage Disease of Systemic *Lupus erythematosus* in the NZB/W F1 Mouse," *Immunopharm. Immunotox.* 22(3):433-449.

To simplify the presentation, we introduce a more streamlined notation that is based on the discussion of the previous page. We write {S0} to refer to the set of signals at time t=0, similarly {S1} means all signal at time t=1, etc. {S0} is a special set as it contains signals at time t=0 as well as signals that come from the control group. The algorithm recursively approximates the probability of model parameters subject to a global optimality condition. I call the algorithm Recursive Probabilistic Pursuit (RPP).

Obtaining the optimal representation for the signals uses the RPP algorithm as well. In the intuitive language, to determine the optimal signal representation, RPP is applied to the row that contains {S0} (previous page). Next, the basis is refined by applying RPP across the rows ({S0},{S1}, etc.), while at the same time we use the constraints defined (left).

The essence of the ideas in this algorithm is used to determine the pattern of metabolite changes (metabolome phase portrait). When constructing the metabolome phase portrait, a different set of probabilistic constraints must be imposed.

Find the optimal representation for the signal set {S0} based on the model for S. The representation results in a basis set B and a set of discrete probability distribution over the range of values for A and f - call this P(A,f).

⇨

Represent the signal set {S1} using the basis set learned from {S0}. This representation results in a probability distribution for A and f. Call this Q(A,f). Recurse over the representation B and refine it so that the mutual information of P and Q, I(P,Q), is minimized.

⇨

Repeat the process with {S2}, {S3}, etc - That is, maximize the mutual information between the signal set, say {S2} and {S0}, but with an additional constraint - minimize the mutual information between consecutive signal sets. The additional constraint does not apply to {S0},{S1}.

⇨

Recurse over the set until average mutual information over the pairwise set of {S0}, {Si} (as above) is maximized while the pairwise mutual information {Si},{Sj} is minimized (as above). We use the final basis set B to specify regions of interest. Roughly speaking, this is the region for which we could not make predictions before the first data set after LPS injection was observed, but could make increasingly better predictions afterwards.

FIG. 3C

G: Glucose
P: Pyruvate
A: Acetyl CoA
F: Fatty Acids
Z: Alanine
T: AcetoAcetate
D: 3-HOB
R: Formate
L: Lactic Acid X: Glycogen/Phospate/Glyceride/Triglyceride
Y: Glycogenic AA/body proteins/ Ketogenic AA

NONINVASIVE MEASUREMENT AND IDENTIFICATION OF BIOMARKERS IN DISEASE STATE

CROSS-REFERENCE TO RELATED APPLICATIONS

This application claims the benefit under 35 U.S.C. 119(e) of U.S. Provisional Patent Application No. 60/896,645 filed on Mar. 23, 2007.

STATEMENT REGARDING FEDERALLY SPONSORED RESEARCH OR DEVELOPMENT

The invention was made with United States government support awarded by NIH GM066326. The United States has certain rights in this invention.

BACKGROUND OF THE INVENTION

The present invention is in the field of identification of disease states by measuring levels of biomarkers that are associated with the disease state.

The complex networks of biochemical processes that underlie living systems are amenable to analysis to determine the state of the living system. For example, under a pathological challenge, there is a shift in these networks as the pathogen affects the system and the system responds to the challenge. For example, various genes involved in different disease processes have been studied and modeled in an attempt to further understand drivers of complex disease states (see, e.g., U.S. Pub. No. 20060241869). As underlying biochemical processes change, there is an attendant change in biological substances that are consumed or produced as the system is challenged. Depending on the specific type of challenge, including bacterial versus viral and different bacterial strains, the levels of different biological substances change. Biological substances that change depending on the pathological condition or "disease state" are referred to as "biomarkers." The invention relies on measuring one or more biomarkers associated with the disease state from a biological sample in order to assess the subject's disease state and specifically address the need in the art for fast and reliable assays of disease states in order to prevent, treat or eliminate infection. Developing a refined biomarker phase portrait platform is useful for early diagnosis of complex diseases with high specificity and sensitivity.

Biomarkers are potential tools for assessing disease state and associated therapeutic decision-making on a patient-by-patient basis. Due to the enormous network complexity underlying biological processes, there is a need in the art for understanding biomarker profiles or fingerprints associated for a specific disease. Without this basic understanding, the vast number of potential biomarkers associated with a disease can overwhelm the ability to rapidly and efficiently determine disease state. There are growing concerns that the rising expenditures in pharmaceutical research and development are not sustainable if sufficient gains for industry or society at large are not realized. Thus, there is a need for development of bioinformatics and associated methods that go beyond the mere collection of massive amount of data. Instead, there needs to be a focused effort on how biomarkers, personalized medicine, and the industry can successfully interact to create feasible clinical solutions. The methods and associated kits presented herein rely on parameterized biochemical pathway models reconstructed from the combination of collected data to provide a richer context in which to interpret associations between metabolite patterns and early disease onset, facilitating more robust points for therapeutic intervention.

Cachexia is a physical condition characterized by weight loss, body wasting and anorexia associated with the host immune response. Cachexia is commonly associated with any one or more underlying disorders such as cancer, infectious disease (AIDs, tuberculosis), and certain autoimmune disorders. Cachexia is a particularly useful pathological condition to model because its underlying biochemical pathways and associated biomarkers have been well-studied (Butz et al. (2006)). Cachexia is readily induced experimentally in animals by injection of bacterial lipopolysaccharide (LPS). The disease is known to be catabolic to muscle tissue and depresses growth via immune stimulation. The basic platform technology of utilizing biomarker profiles as a function of disease state in an assay for assessing disease state in a subject is demonstrated for cachexia.

Immune response to endotoxin has been studied (e.g., Krabbe et al., Clinic. Diag. Lab. Immun. (2001) 8: 333-338). For example, Krabbe et al. shows the change in body temperature, TNF-α, sTNFR-I, circulating monocytes and a variety of interleukin family members after endotoxin administration. Waters et al. (Chem. Res. Toxicol. 2005) discloses NMR-detected changes for a number of substances in urine, blood plasma, renal cortex, and liver in rats following thioacetamide treatment. Those studies, however, do not provide comprehensive information about biomarker profile changes as a function of disease progression, ranging from onset to recovery, required in a commercially-feasible assay of cachexia and related catabolic diseases.

The biomarker profile analysis of the present invention is capable of providing information not currently available in other assays known in the art. For example, because viruses and bacterium have unique effects on certain biochemical pathways, assays relying on measured biomarker profiles provide the ability to distinguish between bacterial and viral infections. This is an important aspect and is needed in the art in combination with rapid and reliable assays order to prevent unnecessary antibiotic use (and attendant bacterial resistance development) for situations where the disease state has a viral origin.

SUMMARY OF THE INVENTION

The invention generally allows for rapid measurement of early onset or progression of disease by identifying and/or measuring a plurality of biomarkers from a biological sample obtained from a subject who is undergoing testing for the disease. Under disease conditions, there is a shift in the normal biochemical pathways as different signals associated with the immune response are up- or down-regulated, and a variety of amino acids are produced and/or consumed. Examining the changes of a variety of biomarkers provides information about the status of the subject from which the biomarkers are obtained. Understanding how biomarkers change (e.g., increase, decrease, no change) with disease progression permits generation of a standard metabolome phase portrait ("MPP") specific for the disease. In particular, biomarker profiles change with disease progression so that by measuring a single biological sample at a single point in time permits verification (e.g., disease or no disease), disease typing, and characterization of a disease state (e.g., early or "onset" versus late or "recovery" phase).

The methodology upon which the invention rests is useful for any of a variety of diseases or other catabolic process. In an aspect, the invention is particularly useful for identifying the state of disease progression, such as onset or recovery, as well as readily distinguishing between bacterial and viral infections, based on the level of each of the biomarkers as well as their trend (increase, decrease or constant) with time. The invention can be combined with other techniques, such as stable isotope ratios naturally occurring in breath (e.g., U.S. Pat. No. 5,912,178), for assessing weather an individual is healthy or in a disease state. Disease states are detected by measuring changes in biomarker levels, and particularly, a plurality of biomarkers interrelated within a biological pathway associated with the disease state. A particular disease state is characterized by detecting and analyzing complex signals from NMR spectra to determine biomarkers whose levels are changing as the disease progresses. This initial disease state assessment allows for "fingerprinting" the dynamic changes associated with disease progression and assists in identifying the nature and current status of the disease progression and process. The methods and materials described herein are particularly suited for use with assays and kits to quickly, reliably, and inexpensively identify disease state. With a disease state condition identified, appropriate treatment regimes can be designed and implemented so as to reduce the disease time course and/or minimize disease outbreak.

In an embodiment, the invention analyzes a biomarker profile within a biological sample obtained from a patient who is being tested for a disease. The specific biomarkers that are measured are determined from an analysis of the key biochemical pathways underlying the disease and the associated host immune response. In an embodiment, a standard biomarker profile is obtained from a healthy individual and from an individual with the disease. Comparing the biomarker profile from the biological sample to the standard biomarker profile (healthy and disease) permits a disease state to be positively identified. Optionally, a second biological sample is isolated from the patient at a second time point or disease progression time point to obtain a biomarker profile trend (e.g., which biomarkers are changing between the first and second samples), thereby providing further information about the disease status or state of the patient.

In an embodiment, the disease state of cachexia is analyzed. In an embodiment, the disease state of sepsis is analyzed. Other biological pathways are amenable to the present metabolic analysis methodology so that other disease states are diagnosed as desired. Depending on the disease state, appropriate action can be employed to assist in decreasing the symptoms of the disease state and assist in decreasing the overall duration and/or magnitude of the disease. The systems disclosed herein are capable of diagnosing any of a number of disease states, such polycystic ovary syndrome (PCOS).

In an embodiment, the invention is an assay or a method for diagnosing a disease state in a subject to-be-tested. The assay comprises detecting the level of a plurality of biomarkers in a biological sample obtained from the subject. The level of each of the plurality of biomarkers permits a biomarker profile to be determined, wherein relative and/or absolute levels of individual biomarkers as well as pooled biomarker types are noted. The biomarker profile is compared to a standard biomarker profile associated with the disease so that disease state is diagnosed. In an embodiment, the disease state is cachexia and the biomarkers are selected from the group consisting of lactate, citrate, formate, acetoacetate, 3-hydroxy butrate, alanine, glutamine, glutamate, valine, isoleucine, leucine, thrionine, lysine and arginine.

Any type of biological sample is used, so long as the sample contains the biomarkers of interest. In an embodiment, the biological sample comprises blood or blood plasma. The samples are optionally further processed to maximize signal noise and improve signal detection.

In an embodiment, cachexia is identified for a biomarker profile comprising one or more, two, three, four, five, six, seven, eight, nine, ten, eleven, twelve, thirteen, or all of: lactate reduction, citrate elevation, formate elevation, acetoacetate elevation, 3-hydroxy butrate elevation, alanine elevation, glutamine reduction, glutamate reduction, valine elevation, isoleucine elevation, leucine is elevated, thrionine elevation, lysine elevation; and arginine elevation. The reduction or elevation is determined by comparing the measured biomarker level to a standard biomarker level or MPP.

In an embodiment, a sample metabolome portrait is determined from the biomarker profile and the disease state is determined by fitting the sample metabolome portrait to a standard metabolome phase portrait, thereby determining the disease state. In this embodiment, the sample metabolome portrait provides a biomarker profile "snapshot" at a single timepoint, this metabolome portrait is fit to a standard metabolome phase portrait generated by controlled experiment and known biochemical pathways as disclosed herein. For example, for an assay for a disease state of cachexia, the standard metabolome phase portrait can obtained from an animal model of cachexia, such as an LPS-injection model in mice, chicken, or mice and chicken.

In an embodiment, the method is repeated for a second biological sample, so that two biomarker profiles are obtained from an individual at two different time points. Identifying individual biomarker changes provides information about the disease state in the individual.

The biomarkers are detected by any means known in the art including, but not limited to, NMR (one-dimensional or two-dimensional NMR), mass spectroscopy, ELISA, microarrays, optical techniques, fluorescence labeling techniques, flow cytometry, chromatography, high pressure liquid chromatography, capillary electrophoresis, chemical or biochemical sensors. Chemical sensor is used broadly to refer to devices capable of providing a quantitative or semi-quantitative measure of a chemical, and specifically a chemical that is a biomarker.

In an aspect, 1D NMR is used for partial identification and/or semi-quantification of metabolites or biomarkers. 2D NMR is optionally used to further investigate the status of metabolites or biomarkers. For example, if the 1D-spectrum contains crowded or overlapping peaks, making biomarker identification difficult, 2D NMR provides a means for verifying the identity of biomarkers or compounds. In addition, 2D NMR provides a means for confirming and calibrating the semi-quantitated biomarker values. In an aspect, the invention provides identification of relevant biomarkers (including a subset of biomarkers or clique) for a disease state, such as by mathematical algorithms disclosed herein on a biomarker profile or biomarker metabolome phase portrait, for a disease state and/or quantification or semi-quantification of the biomarkers. "Semi-quantification" refers to the relative amount of biomarker, such as whether a biomarker is increasing or decreasing with time, as well as whether a biomarker is at different level compared to another biomarker.

In an embodiment, any of the disclosed methods and assays further involves determining a disease state progression. For example, whether the disease state is an early or onset stage versus a later recovery phase is determined by identifying where on the MPP time course the measured biomarker profile lies.

Because a pathology that is viral- or bacterial-based generates detectable difference in biomarker profile, any of the methods can be used to determine whether the disease state is associated with a viral infection or a bacterial infection. Because the disease state of cachexia involves fundamental biochemical pathways that are conserved across species, the invention is useful for assessing disease state in any of a number of different animals. The results from a plurality of animal models show the cachexia response is a conserved response. In an embodiment, the subject is a mammal. In an embodiment, the subject is selected from the group consisting of poultry, bovine, swine, horse, sheep and human.

In an embodiment, the invention is a kit for assessing a disease state in a biological sample. The kit includes a means for measuring an amount of a plurality of biomarkers associated with the disease state. Means for measuring an amount of a plurality of biomarkers includes any one or more of techniques known in the art such as spectroscopy (e.g., NMR spectroscopy, mass spectroscopy), ELISA, radioactive isotope replacement. Also provided is a standard metabolome phase portrait for the disease state (or information related thereto), wherein the standard metabolome phase portrait comprises changes in the relative amount of biomarkers as a function of disease progression. This standard MPP provides the basis for determining disease state by comparing the measured biomarker profile to the standard MPP. Means for identifying the disease state based on a comparison of the measured biomarker profile and the standard metabolome phase portrait spans relatively simple devices such as written instructions or tables for matching a profile pattern to a disease state, to algorithms incorporated with the biomarker profile output for automated fitting of the biomarker profile to the MPP. For example, a computer connected to the biomarker measuring device provides rapid and accurate capability of diagnosing the disease state.

In an embodiment, the comparison between the measured biomarker profile and the standard MPP is by mathematical fitting of the amount of each biomarker to the standard metabolome phase portrait. Any of the kits or methods disclosed herein may be used for a disease that is cachexia. In an embodiment, the kit measures one or more biomarkers selected from the group consisting of lactate, citrate, formate, acetoacetate, 3-hydroxy butrate, alanine, glutamine, glutamate, valine, isoleucine leucine, thrionine, lysine and arginine. In an embodiment, the standard metabolome phase portrait is from an LPS-injection model of mouse, chicken, or mouse and chicken.

In an embodiment, a method of treatment of the disease state is provided based on the result(s) of the diagnosis from the kit or methods of the present invention. For example, for a disease state of bacterial origin, the subject can be prescribed appropriate antibiotics. If the disease state is viral, the use of antibiotics is avoided. Treatment is further refined by determining whether the disease state is beginning or has peaked and is starting to recover. In general, early disease states tend to be conducive for disease transmission relative to later-stage disease states. Accordingly, the invention optionally provides information regarding the likelihood of disease transmission and so isolation and/or sterile steps are taken as appropriate to minimize further disease transmission. Treatment includes whether drugs or other chemical compounds should be administered, including the kind, amount and duration of drug administration, as well as patient isolation and appropriate aseptic methods to minimize disease transmission.

In an embodiment, the method of diagnosing a disease state in a subject relates to detection of one or more cliques. A "clique" refers to one or more biomarkers that are related to a pathway such as a lipid, carbohydrate, ketogenesis, immunoreactivity or toxicity pathway indication, for example. Depending on the disease state being tested for, a clique is chosen accordingly. Pathway can also refer to the direction the pathway is being driven, e.g., metabolism or catabolism, activation or inactivation. Furthermore, a clique can be further subdivided into a subclique, wherein biomarkers within the clique are subgrouped to provide further detailed information regarding pathway dynamics, for example, wherein certain biomarkers may be elevated or depleted. One example of a clique of interest is those biomarkers that provide an indication of toxicity or infection and include: citrate elevation, formate elevation, acetoacetate elevation, and 3-hydroxy butrate elevation, for example.

In an aspect, the method detects one or more cliques at one or more different time points. For example, two separate biological samples are obtained at two different times from a subject being diagnosed for a disease state. A clique profile is determined by measuring each of the biomarker levels within that clique at each time point. The disease state is determined by comparing the clique profiles to a standard reference, or by comparing clique profiles at different time points, or both. In an aspect, the two or more cliques are related to different pathways. In an aspect, the cliques are selected from a pathway that relates to toxicity, lipids, carbohydrates, ketogenesis, and immune response.

BRIEF DESCRIPTION OF THE DRAWINGS

FIG. 3C is a flow-chart representation of a Recursive Probabilistic Pursuit (RPP) algorithm to determine patterns of metabolite changes, taking into account natural variability of biomarker levels within and between individuals.

DETAILED DESCRIPTION OF THE INVENTION

Figure 1:
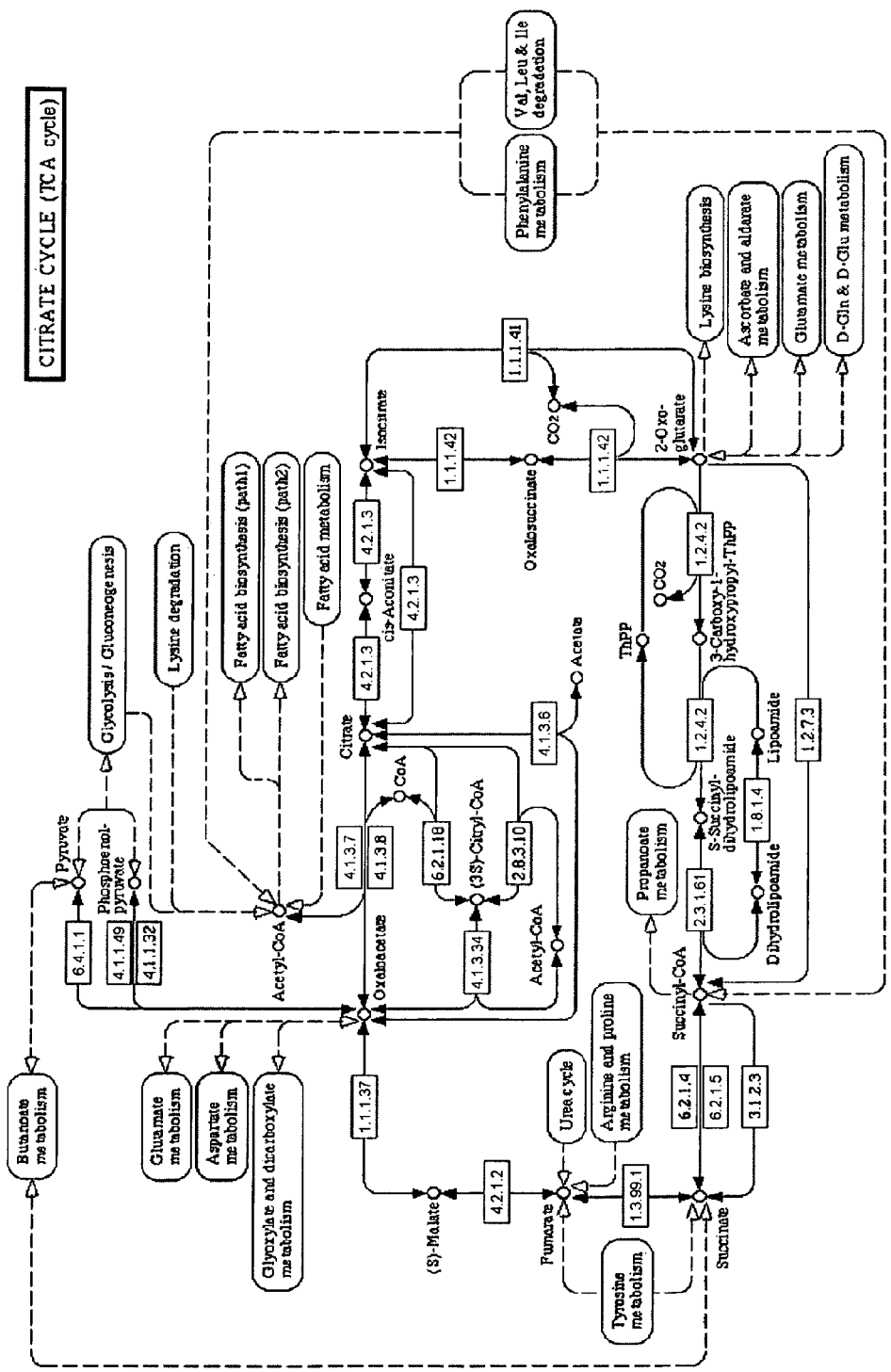
FIG. 1 summarizes multiple metabolic pathways involved in the TCA cycle that form a highly variable and complex multi-parameter system.
Figure 2A:
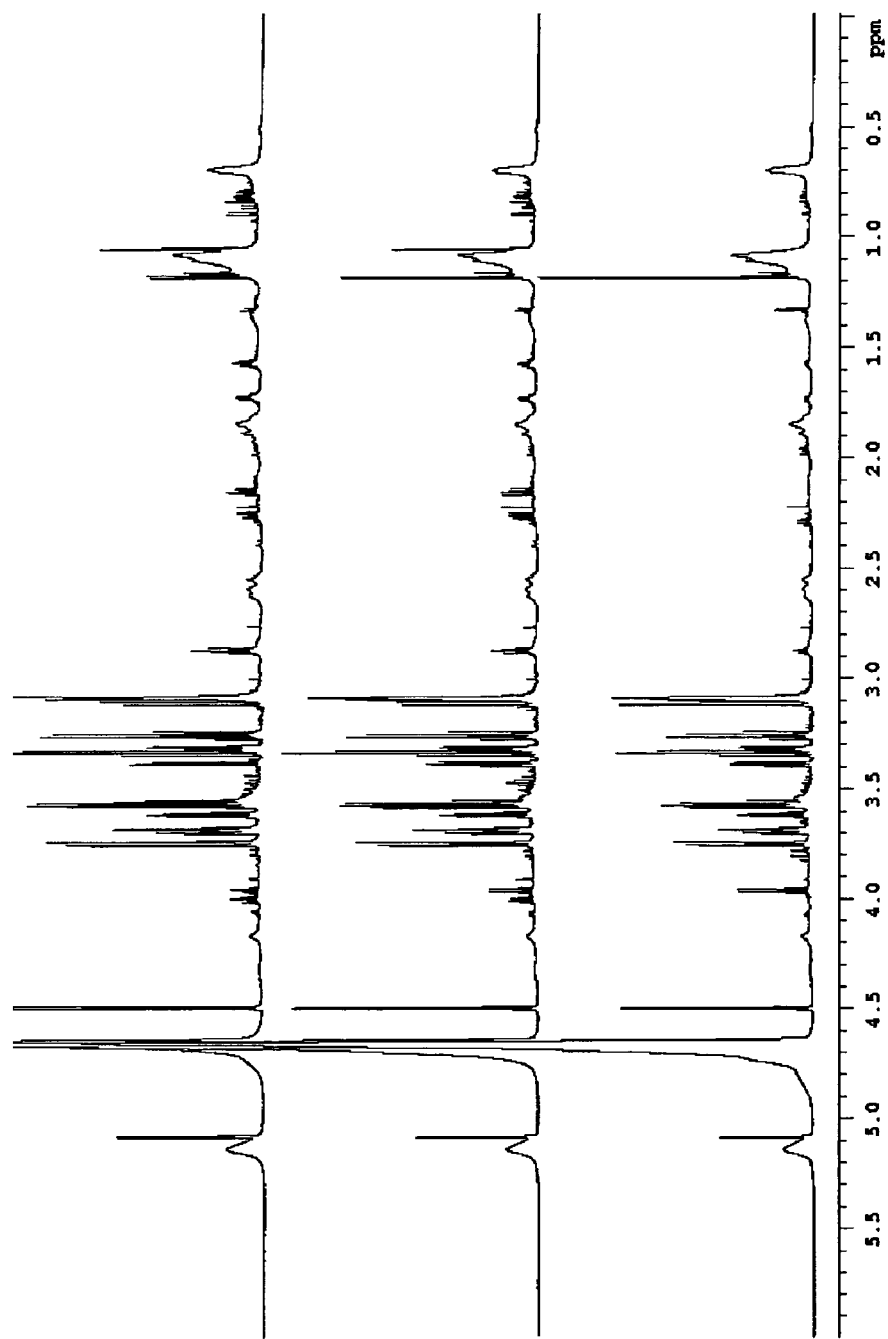
FIG. 2 contains NMR plots obtained from a biofluid sample at three different time points. Change in peaks is associated with changes in biomarkers.
FIGS. 2B and 2C are close-up views of the spectra shown in 2A and more clearly show changes in particular peaks.
Figure 2B:
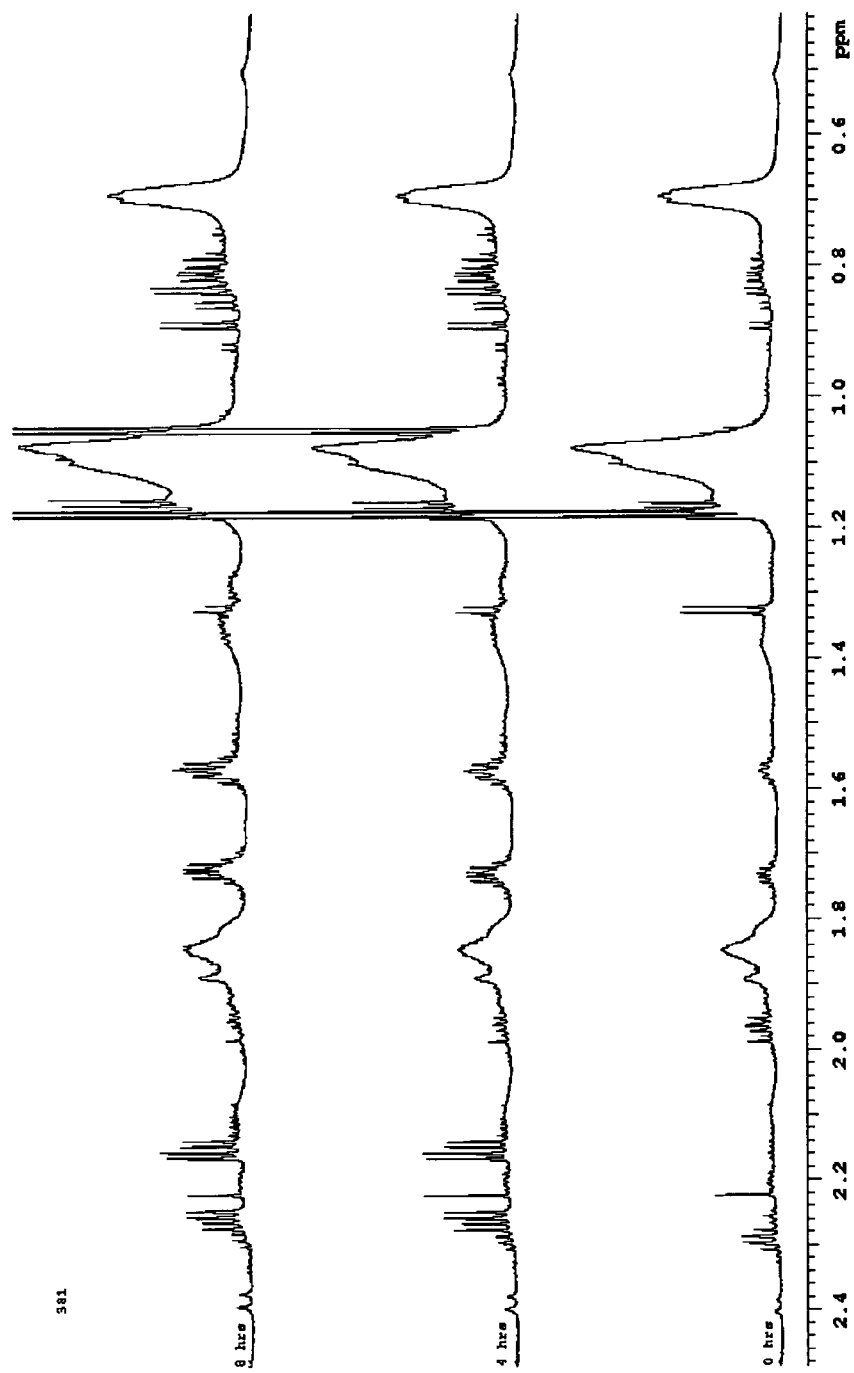
Figure 2C:
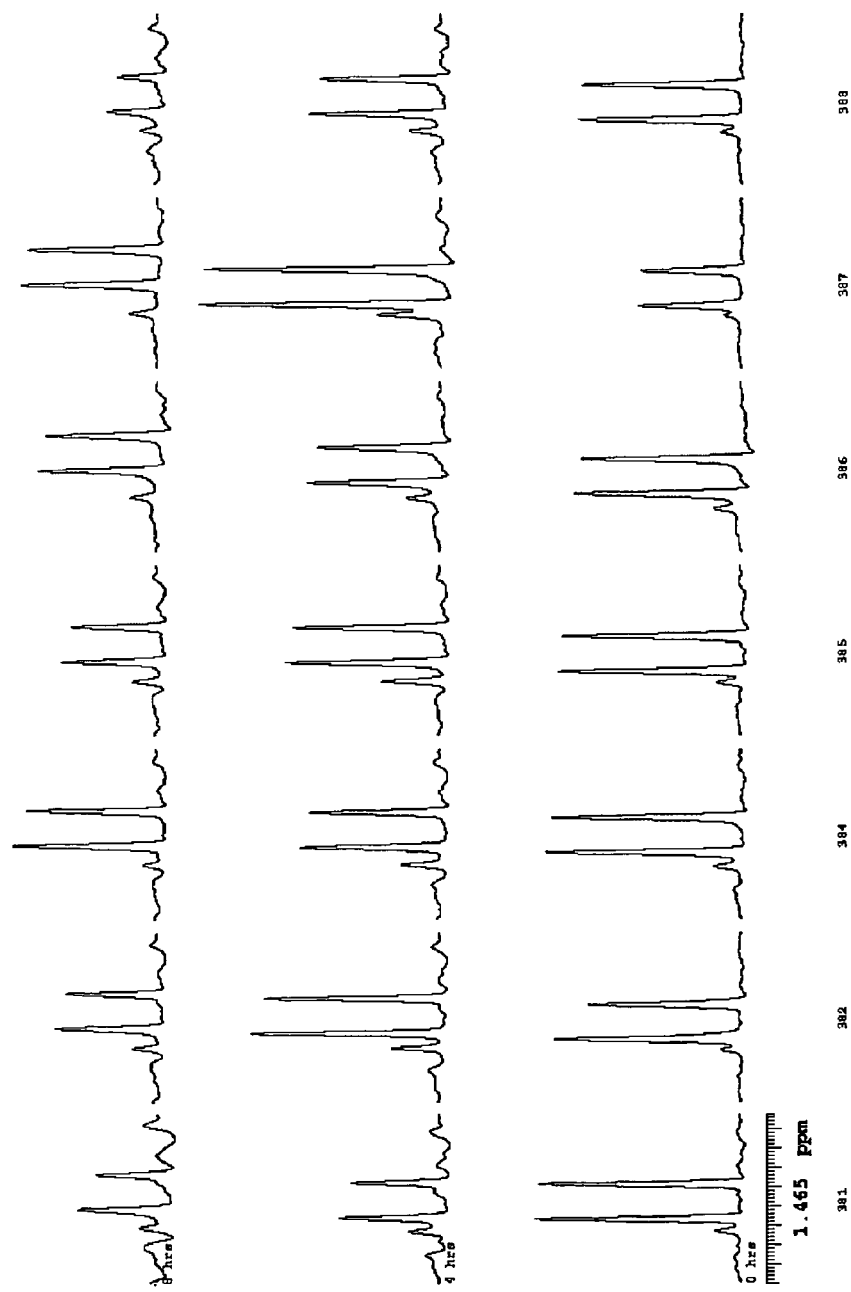

"Disease state" broadly refers to whether an individual is positive or negative for a pathogenic condition. In an aspect, disease state refers to specific disease types such as cachexia, as well as whether the disease has a viral or bacterial origin. "Disease progression" is a specific aspect of disease state that particularly refers to the time-course or progression of the disease state. Treatment regimes can be more specifically tailored depending on whether the disease state is in its early (e.g., "onset") stages or later (e.g., "recovery") stages.

"Biological sample" refers to isolation of tissue and/or fluid from a subject that is being tested for a disease state. Any biological sample can be used by the present invention, so long as the sample contains the biomarkers for the disease state being tested, such as blood, blood components, urine, saliva or breath. Preferred biological samples include blood or blood plasma.

"Biomarker" refers to biological compounds that are involved in one or more biological pathways that are associated with the disease state. Accordingly, for infections, the biomarker can be involved with pathways that regulate the host immune response. For a wasting and anorexia disease resulting from immune stimulation such as cachexia, the biomarkers can include various inflammatory mediators, and amino acid metabolites and/or catabolites associated with muscle breakdown. A "profile" of biomarkers or "biomarker profile" refers to the amount or concentration of two or more biomarkers. Such a profile provides useful top-level "fluxomics" information about whether certain types or pools of biomarkers are elevated or depleted. A disease state can have a specific biomarker profile, and more particularly a time-dependent biomarker profile. Accordingly, the biomarker profile is also referred to as a disease state "finger-print" that permits the identification of a disease state based on a measured biomarker profile. A biomarker that is "related to the disease state" refers to biomarker profiles that change depending on the disease state and provides a means for assessing a subject's disease state based on the measured biomarker levels.

A "standard biomarker profile" refers to the fingerprint that is generated by a disease state and is useful for assessing whether or not a measured or determined biomarker profile is positive or negative for the disease state. Such standard profiles are obtained from subjects confirmed to have the disease state by other means known in the art (e.g., cultures, antibodies, etc.) or animal models known to mimic the disease state. For example, the disease state of cachexia is induced experimentally by injection of bacterial lipopolysaccharide ("LPS"). Klasing et al. (1984) Proc Soc Exp Bi9ol Med. 176:285-91; Sharma et al. (1992) Am J Physiol Regul Integr Comp Physiol 262:R786-93; Butz et al. (2006) J Nutr Biochem. 17(11):735-41. The metabolome phase portrait for a cachexia model is preserved across chicken and mice, in agreement with the observation that acute inflammation is conserved across species. In an aspect, the standard is an external, internal, or both reference. "Internal reference" refers to a standard obtained from the subject. "External reference" refers to a standard that is obtained from a control subject who is not the one being currently tested, and optionally is from a different animal species.

Biomarker "reduction" or "elevation" refers to measured biomarker levels being changed relative to a standard biomarker level from a standard biomarker profile. Alternatively, the reduction or elevation can refer to changes in biomarker levels from two biological samples obtained from a subject at different times (e.g., potentially different disease progression time points).

Figure 14:
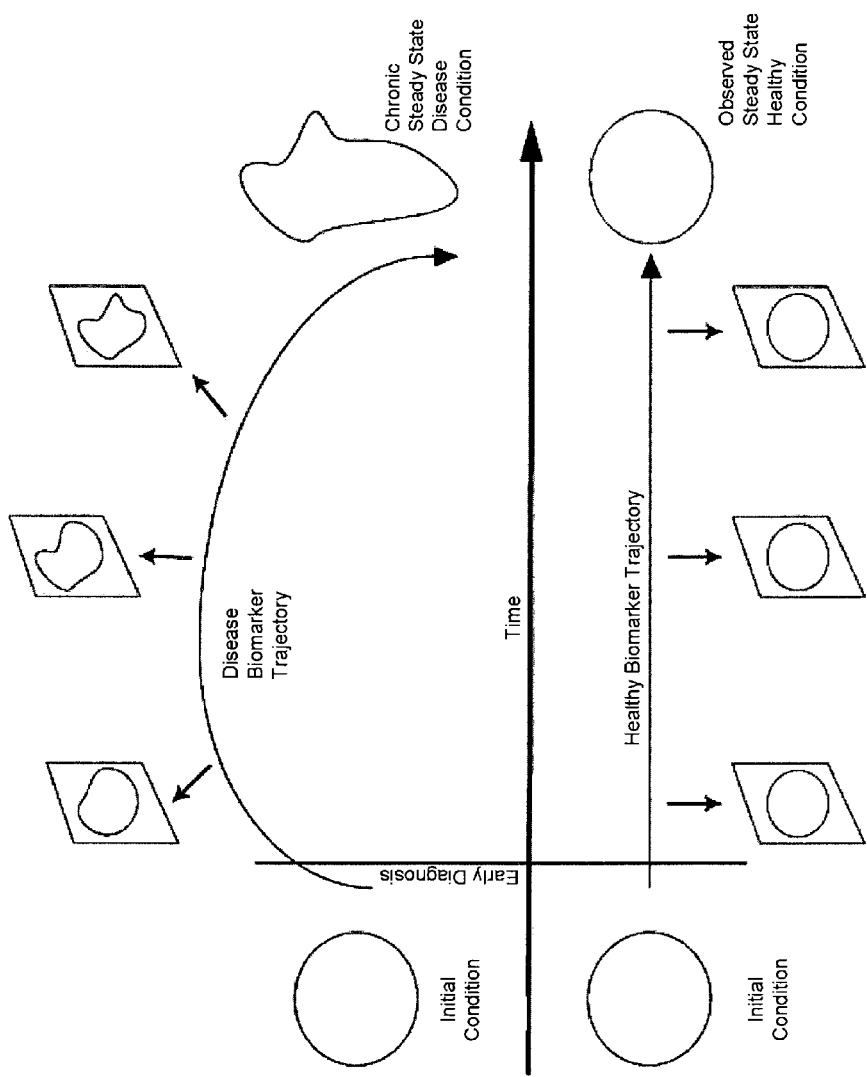
FIG. 14 illustrates metabolic progression of healthy and disease biomarker trajectory over the course of disease from onset to chronic and steady-state condition. For certain pathogenic conditions, an individual's immune response is capable of bringing the biomarker trajectory back to an initial state (e.g., "healthy").

A series of measured biomarker profiles, each corresponding to a disease state progression time point, are combined to generate a "sample metabolome phase portrait." A "sample metabolome portrait" corresponds to a single time-point biomarker profile. Similarly, a series of standard biomarker profiles are combined to generate a "standard metabolome phase portrait", as exemplified in FIG. 14.

As used herein, the step of "comparing the profile" includes qualitative and/or quantitative comparisons. A qualitative comparison includes relatively simple comparisons such as whether a biomarker has a higher, lower, or equivalent value compared to the standard. Quantitative comparisons include curve fitting, algorithms and other quantitative methods known in the art. Such comparisons facilitate "diagnosing" the disease state. Diagnosing refers to determining whether the sample is positive or negative for the disease state, and optionally the disease state progression and/or further information such as whether the disease state has a bacterial or viral origin.

All references cited throughout this application, for example patent documents including issued or granted patents or equivalents; patent application publications; and non-patent literature documents or other source material are hereby incorporated by reference in their entireties, as though individually incorporated by reference, to the extent each reference is not inconsistent with the disclosure in this application (for example, a reference that is partially inconsistent is incorporated by reference except for the partially inconsistent portion of the reference).

Every formulation or combination of components described or exemplified herein can be used to practice the invention, unless otherwise stated. All patents and publications mentioned in the specification are indicative of the levels of skill of those skilled in the art to which the invention pertains. References cited herein are incorporated by reference in their entirety to indicate the state of the art as of their publication or filing date and it is intended that this information can be employed herein, if needed, to exclude specific embodiments that are in the prior art. All tables attached hereto (e.g., Tables 1-2) are part of the specification.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein may be practiced in the absence of any element or elements, limitation or limitations which is not specifically disclosed herein.

One of ordinary skill in the art will appreciate that starting materials, materials, reagents, synthetic methods, purification methods, analytical methods, assay methods, and methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention involves the identification of biomarker profiles or biopatterns, as well as metabolome portraits, that indicate a condition of interest, such as a disease. The progression of a disease is a very complicated biological process that can impact multiple biochemical pathways throughout the body, including those associated with metabolic/catabolic processes as well as factors that regulate the host immune response. In particular, changes in a biochemical pathway are evident as changes in the different biomolecules within that pathway. Accordingly, the present invention relies on assessing a condition by measuring paramater changes in the system, such as changes in relevant biomarkers associated with the system. By identifying concomitant changes of multiple biomarkers, useful information is obtained as to the disease state.

BIOCHEMICAL PATHWAYS. Metabolic pathways are complex multi-paramater systems having a large number of constituents with complex interaction between constituents such as positive and negative feedback loops. An example of one important metabolic pathway is the Krebs cycle (TCA, tricarboxilic acid, citric acid) summarized in FIG. 1. Major biochemical pathways that have carbohydrates, proteins or lipids as substrate and product are an integral part of the TCA cycle. The TCA cycle has been extensively studied since its original discovery and is complex, comprising multiple biochemical pathways. Glucose is the primary precursor for the TCA cycle. Under normal healthy conditions, there is a balance between how much glucose is consumed from available food through the TCA cycle whose primary function is generating necessary energy for body. Excess amount of available glucose is converted to amino acids (to make new proteins), glycogen (complex carbohydrate), and lipids. This condition is called the anabolic state and is identified as a net accretion of body mass.

In a disease (catabolic) state (marked by weight/muscle loss or wasting) various interacting pathways disturb the balance in the TCA cycle. For example, with onset of disease a catabolic state causes the body to consume its own resources such as proteins, carbohydrates, and lipids. In this case, due to muscle loss, protein breakdown becomes rapid which results in an increase in amino acid availability for making new antibodies (i.e new proteins to be used for defense mechanism), or metabolizing excess amino acids for energy production. Amino acids are categorized as essential (obtained only from food) and nonessential which can be further categorized as either ketogenic or non-ketogenic. Metabolism of each category is different due to complex interacting pathways and their requirements for many different functions in body. Increased or decreased levels of various amino acids or their derivatives indicate affected pathways. Such changes are carefully interpreted with changes seen due to disease versus normal conditions. In this manner, a disease state is identified based on its underlying biomarker profile.

Major small molecule metabolites that can be identified by NMR spectroscopy are various intermediates and derivatives from protein, lipid, and carbohydrate metabolism. These metabolites are transient indicators of how the body is consuming self under disease condition versus normal healthy condition. After onset of disease, dynamics and magnitude of changes of metabolites in a time dependent manner provide excellent markers for following disease progression and identification of a fingerprint or biomarker profile that is characteristic of a given disease.

Figure 17A:
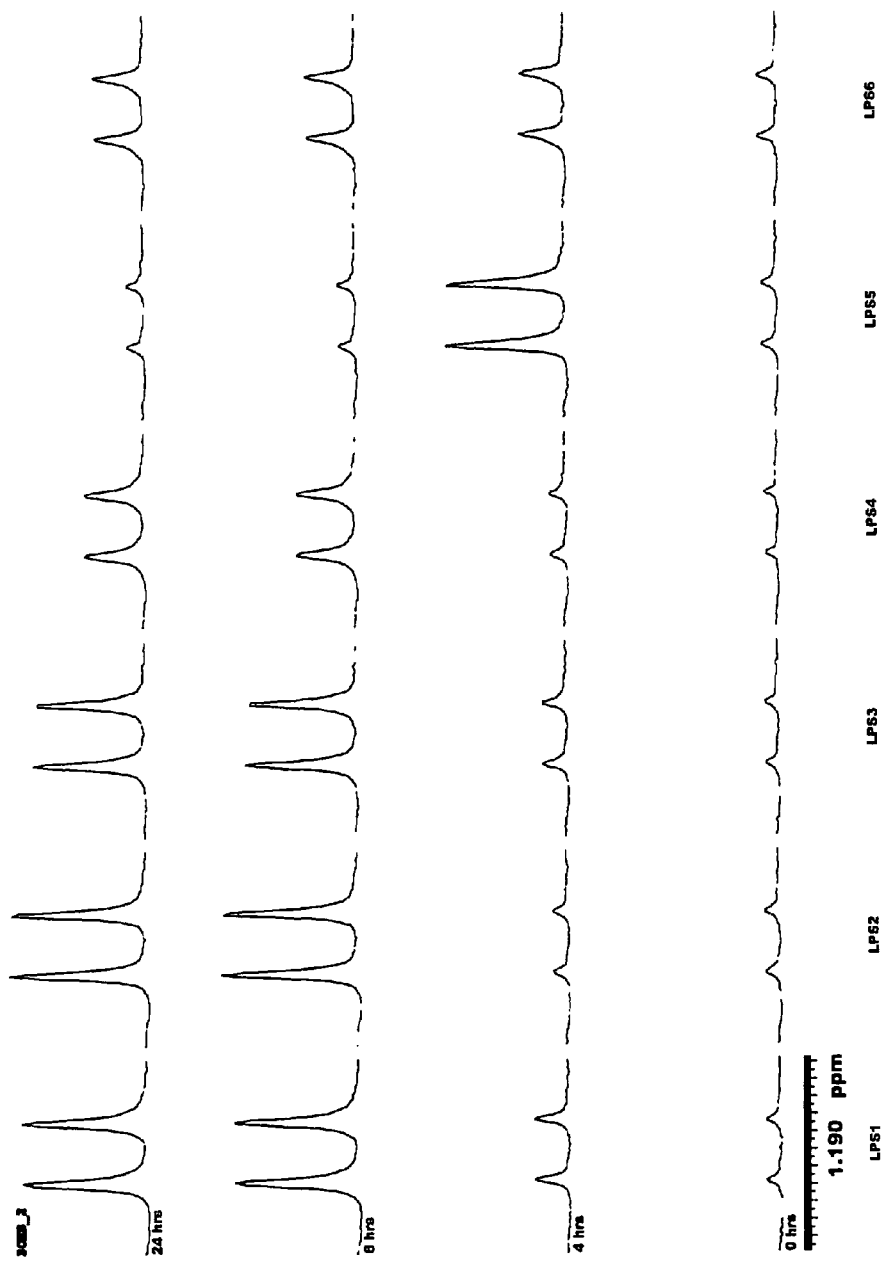
FIG. 17A is NMR spectra of changes in six LPS treated mice (left to right traces, labeled LPS1-LPS6) for 3-OH B metabolite, with increasing time from bottom to top (0, 4, 8 and 24 h). Increasing signals for 4 and 8 hrs indicate individual immune response time and dynamics. B. Control saline treated mice (left to right traces for three experiments, saline1-saline 3) with increasing time from bottom to top.
Figure 17B:
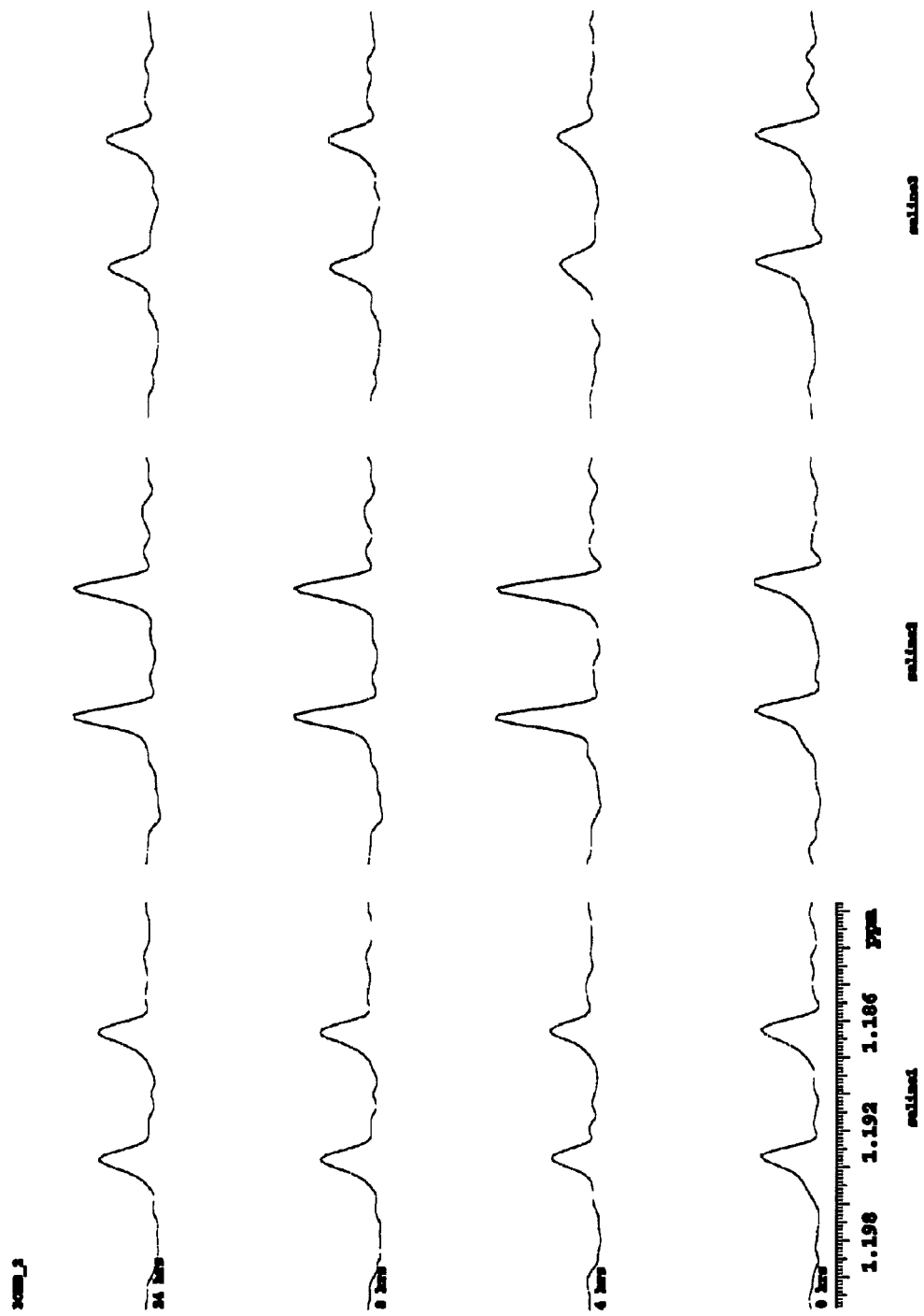

The invention uses various novel methods to achieve biomarker interpretations for diagnostic purposes, including: 1) Data extraction methodology with state-of-the-art mathematical methods. 2) Comparison of time-dependent plasma samples by NMR spectroscopy for both healthy and LPS-injected groups to gain information about dynamics of metabolites due to induction of inflammation. The normal variation present among and within individuals increases the difficulty in interpreting biomarker levels and disease state. 3) The specialized analysis methods presented herein overcome this obstacle. Broad understanding and correct interpretation of various biochemical processes and pathways are essential in defining biomarkers relevant to disease. The results of the experiments provided herein indicate that the same molecules are changing within the LPS-induced group, however, they vary in their temporal profiles. Some individuals respond to inflammation faster than others. For example, FIG. 17A summarizes changes in 3OH-B metabolite as a function of time for six individuals. They produce certain metabolites faster and reach recovery state sooner. Others fall behind and follow similar changes at slower rates. The overall pattern of biomarker changes across all individuals with time indicate that the observed changes are due to inflammation rather than individual variations. The control experiment in FIG. 17B indicates that 3OH-B remains at a steady-state value without variation for each individual examined.

The biochemical pathways associated with the endotoxemia/cachexia models interact in a complex and dynamic fashion. With disease onset, transient changes of metabolites occur over time until recovery when "dynamic equilibrium" is reached. Since variations among individuals exist both in their response to disease and normal experimental variations (peak positions slightly varies among samples due to sample preparation) each individual is used as his/her own control to minimize some of the variation. Observations indicate that the following metabolites change within the first 4 hours of onset of infection in chickens: Lactate (Lac, decreased), citrate (increased), formate (increased), acetoacetate (ACA, increased), 3-hydroxy butrate (3-OHB, increased); nonessential amino acids: alanine (Ala, increased), glutamine (Gln, decreased), glutamate (Glu, decreased); and essential amino acids: valine (Val, increased), isoleucine (Ile, increased), leucine (Leu, increased), thrionine (Thr, increased), lysine (Lys, increased), arginine (Arg, increased). The same experiment is conducted in mice and a similar pattern for most metabolites is observed (FIG. 13). Similar trends for both mice and chicken suggest that the response to LPS-injection (e.g. cachexia) is conserved across species. The increased level of essential amino acids indicates protein catabolism (protein break down). In addition, both Leu and Thr are ketogenic amino acids (i.e. they are products of fatty acid metabolism or break down). Nonessential amino acids such as Ala, Gln and Glu decrease due to normal metabolism through TCA cycle and further catabolism. Most of these metabolites are observed in mice. After 4 hours, these metabolites approach their steady state levels and completely recover by 24-48 hours with metabolite profiles similar to the healthy group (see Tables 1 and 2; FIG. 13). These recovery periods in the metabolome are consistent with animal growth responses after LPS-induced inflammation (Butz et al., 2005).

Infection caused by LPS results in macrophage breakdown and production (increased level) of 3-OHB. Important metabolites that reflect infection state are formate, 3-OHB, citrate and ACA. These are all "ketone bodies" which indicate protein break down or "self-consumption". Fatty acid break down also causes acetyl coA production which results in similar types of ketogenic metabolites. These metabolites are also observed in mice plasma samples due to LPS-induction which indicates conservation of similar pathways across species. In humans, measles caused increased level of hydroxybutrate (2 and 3-OHB), along with AOA and acetone, indicating macrophage breakdown and an infection state (Kano, K. and T. Ichimura, Increased alpha-hydroxybutyrate dehydrogenase in serum from children with measles. Clin. Chem., 1992. 38(5): p. 624-7). In addition, this metabolite is also identified as a reliable indicator of diabetic ketoacidosis in children (Bedside Monitoring of blood b-hydroxybutyrate levels in the management of diabetic ketoacidosis in children. A. Rewers, et al. Diabetes Technology and Threrapeutics, 2006, 8: p671-676).

Because the pathways involved in biological systems are extremely complex open systems, subject to individual variability based on conditions that are hard to model, it is difficult if not impossible to obtain a simple, straightforward and absolutely certain prediction based on a given biopattern. Instead, the models function to reduce possibilities and use probability pools to develop reliable biopattern dynamics and diagnostics.

Biomarker Identification: In order to obtain a metabolome phase portrait for a disease state, reliable and quantitative methods for identifying and measuring a plurality of biomarkers are used. A number of NMR and mass spectrometric techniques are employed. $^1$H NMR spectroscopy is a useful technique in that it requires minimal sample preparation, while allowing for analysis of a wide range of compounds. In addition, the method can be applied with little prior sample composition knowledge. Because NMR is non-destructive, multiple experiments can be performed on the same sample including one- and two-dimensional NMR experiments, such as homonuclear ($^1$H-$^1$H), or heteronuclear ($^1$H-$^{13}$C) correlations to permit more definitive identification and characterization of biomarkers. These experiments are complemented by MS, which is better for identifying specific biomarkers by measuring low concentration metabolites and determining accurate molecular weights.

Quantitative MS analysis requires special consideration, and several different strategies are employed for metabolite samples. Absolute quantification generally relies on addition of an internal standard. It is, however, impractical to add an internal standard for every analyte in a comprehensive metabonomics analysis. This issue is addressed by developing an isotopic labeling approach that enables relative quantification of broad ranges of analytes within a given functional class [Shortreed et al., 2006 Anal Chem 78:6398]. Relative concentrations are determined by labeling one sample with an isotopically light reagent and another sample with an isotopically heavy reagent and then mixing the two samples prior to liquid chromatography (LC)-MS analysis. Methylacetimidate and formalin are developed as molecular labels for relative quantification of amines, and cholamine is developed for relative quantification of carboxylic acids (see U.S. Pat. No. 5,912,178). The reactions between metabolites and labels proceed essentially to completion with little or no unlabeled compounds detected after labeling. These labeling reagents all yield chemical products readily ionized under the normal acidic conditions commonly used in positive-mode electrospray ionization LC-MS. Furthermore, all of them enhance ionization efficiency and concomitantly lower the detection limits of the compounds studied. These labeling strategies are successfully applied to several sample types including: seeds, plant tissues, blood plasma, egg lipids, cell extract and cell media.

NMR and MS data analysis. High-resolution NMR spectroscopy is a powerful technique for examining metabolic variations in response to environmental perturbations, including by a pathogen. To obtain relative quantitative information, these studies compare NMR signal intensities of control samples and treated or exposed ones. However, analysis of NMR data from complex biological samples presents challenges arising from variations of peak shape and positions due to changes in sample condition, which obscure the process of pattern discovery. To compensate for these changes, methods are used, including algebraic approaches (inversion of Hankle matrix), a host of warping techniques, and similar methods, as well as statistical and heuristic methods. This work applies to the similar problem that arises in LC-MS due to variations in retention times from chromatogram-to-chromatogram. Due to the massive amount of data generated by MS or NMR signals, the early data extraction is performed in a robust and unbiased fashion. Extracted data must parsimoniously satisfy a number of constraints at the same time as solving the inverse problem. These constraints include models of metabolic changes, fluctuations arising from phenotypic variations, temporal pattern of changes, and other noise inherent in a complex system. These requirements in the phase portrait methodology are addressed as described below.

NMR spectra (1D) are collected rapidly and thus they are ideal for studying a large set of samples. 1D spectra are crowded, however, and the variations mentioned above seriously confound the detection of important signals. Therefore, 2D NMR data collection is often necessary in order to identify and quantify the important biological signals. For large sample sets, both the collection and analysis of 2D NMR data are highly challenging. The process is optimized by using 1D data to identify important regions of signal variation. Once important regions (as well as their probability or significance) are identified, the search and identification of metabolites within the specified regions is rapid and efficient. Furthermore, once the signals of interest are identified, their resolution and assignment, within 2D data sets collected for a small subset of the samples, are accomplished quickly. On the basis of having assigned the key signals in the data subset, the larger 1D data set is studied statistically for unbiased sampling Phase Portraits. Certain mathematical frameworks have gained acceptance in the systems biology community, particularly for the study of metabolism. One approach that uses constraint-based modeling imposes physico-chemical constraints on the metabolomics network to determine a feasible solution space in which the system must operate instead of attempting to calculate an exact phenotypic solution. One advantage of this method is that models and experimental data are more easily reconciled and studied on a whole-cell or genome-scale level. Other successful applications of these concepts include constrained models in conjunction with the second law of thermodynamics. To become the driving force in the biological discovery process, however, these approaches require detailed and lengthy examination of dynamic states of the metabolic system. This in turn requires a reasonably complete knowledge of aspects of the system in order to select correct models and data subsets. Experimental data sets must first be examined for their consistency against the underlying biology and chemistry represented in the models and then further tested and validated in the context of models to gain understanding of metabolism. Unfortunately, traditional approaches do not currently fully enable identification of the key underlying biological mechanisms and thus do not allow generation of robust hypotheses which are subsequently tested experimentally.

NMR and MS provide point-in-time measurements of metabolites, dynamic analysis of breath samples offers a real-time and global signature of some aspects of the metabolism. Dynamic data are used to reveal responses to perturbations that are not otherwise detectable. Furthermore, in complex diseases reverse engineering of biological networks take on a fundamental role. The phase portrait platform provides a probabilistic approach (see FIG. 3) to the identification of significant parameters of the biological network. To develop the metabolome phase portrait for a disease, a combination of NMR, MS and CRDS techniques to collect complementary data from plasma, urine, saliva, and breath are used. The metabolome phase portrait for cachexia is determined from a mouse and a chicken model from plasma by a combination of NMR techniques.

For our analysis, we consider the following data set. At various time points, a number of samples have been collected and spectra that conveys the metabolome profile of the samples has been collected. The samples may include data from a control group. We consider the control group data, along with the data at time t=0, as indicators of "natural variability." It is not necessary to have the same number of spectra at each time point. The signals are denoted by $S_{ti}$, where t is a discrete index for time and i is a second discrete index that identifies a specific signal at time index t. Each signal S is modeled as the finite sum of decaying exponentials plus noise. $A_j$ and $f_j$ are complex, and along with the number of signals n, are initially unknown:

$$S = \sum_{j=0}^{n} A_j \exp(f_j).$$

Figure 3A:
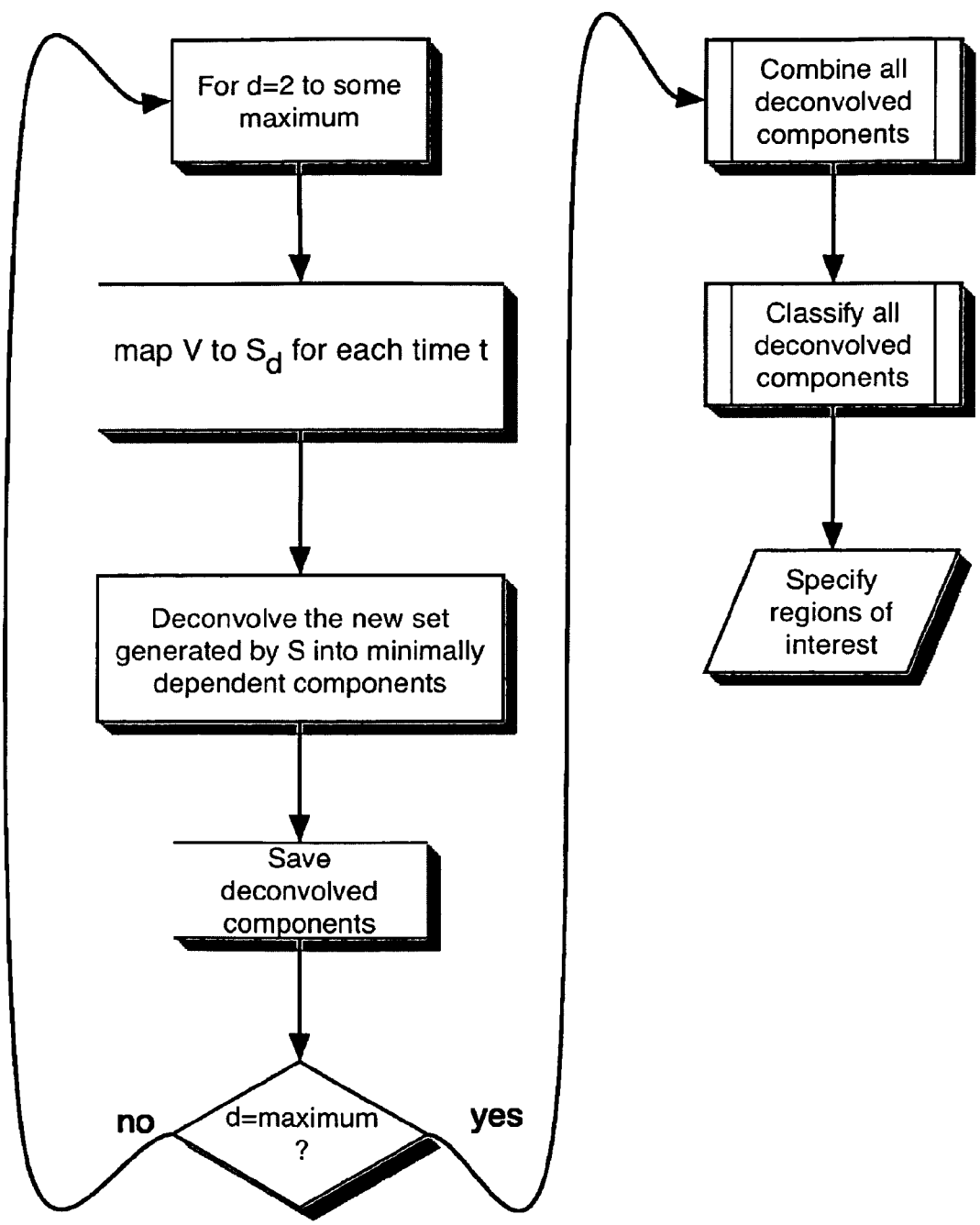
FIG. 3A is a flow-chart summary of the methodology used to classify whether signals associated with a putative biomarker are changing or unchanging.
Figure 3B:
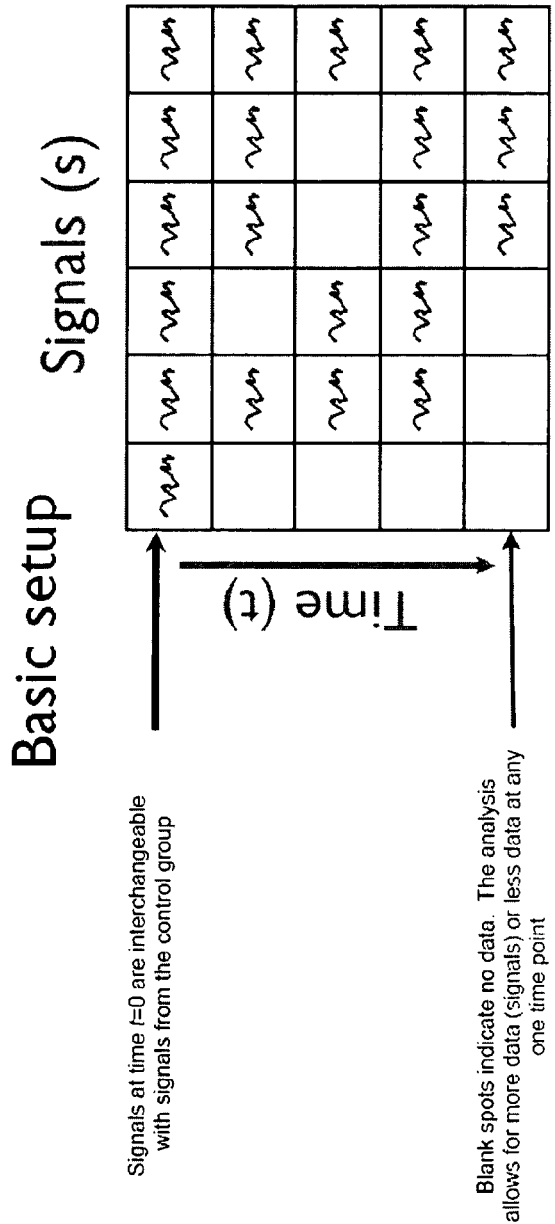
FIG. 3B summarizes an algorithm to identify biomarkers associated with a disease state by a probabibilistic analysis of a metabolome profile.

Noise is not modeled and is not assumed to be Gaussian. The goal of the probabilistic analysis algorithm is to find ranges for the complex part of the f where the corresponding $A_j$ vary in time with a "high degree of predictability." The algorithm described in FIG. 3C is not dependent on a specific model—other models could be selected, for example for mass spectroscopy.

Labeled metabolites produce an isotopic signature in MS data that is readily identifiable. Relative quantification of metabolites is achieved by calculating the intensity ratio for each isotopic pair identified by our software. Neutral masses are calculated by subtracting the mass of the label from the mass-to-charge (m/z) value. These masses are submitted to existing metabolite databases for potential identification. The nature of the labeling is to target an individual functional group (either amines or carboxylic acids at this time), thus the identification is made easier by this knowledge. The pattern of isotope ratios serves as an input to the phase portrait.

Figure 15:
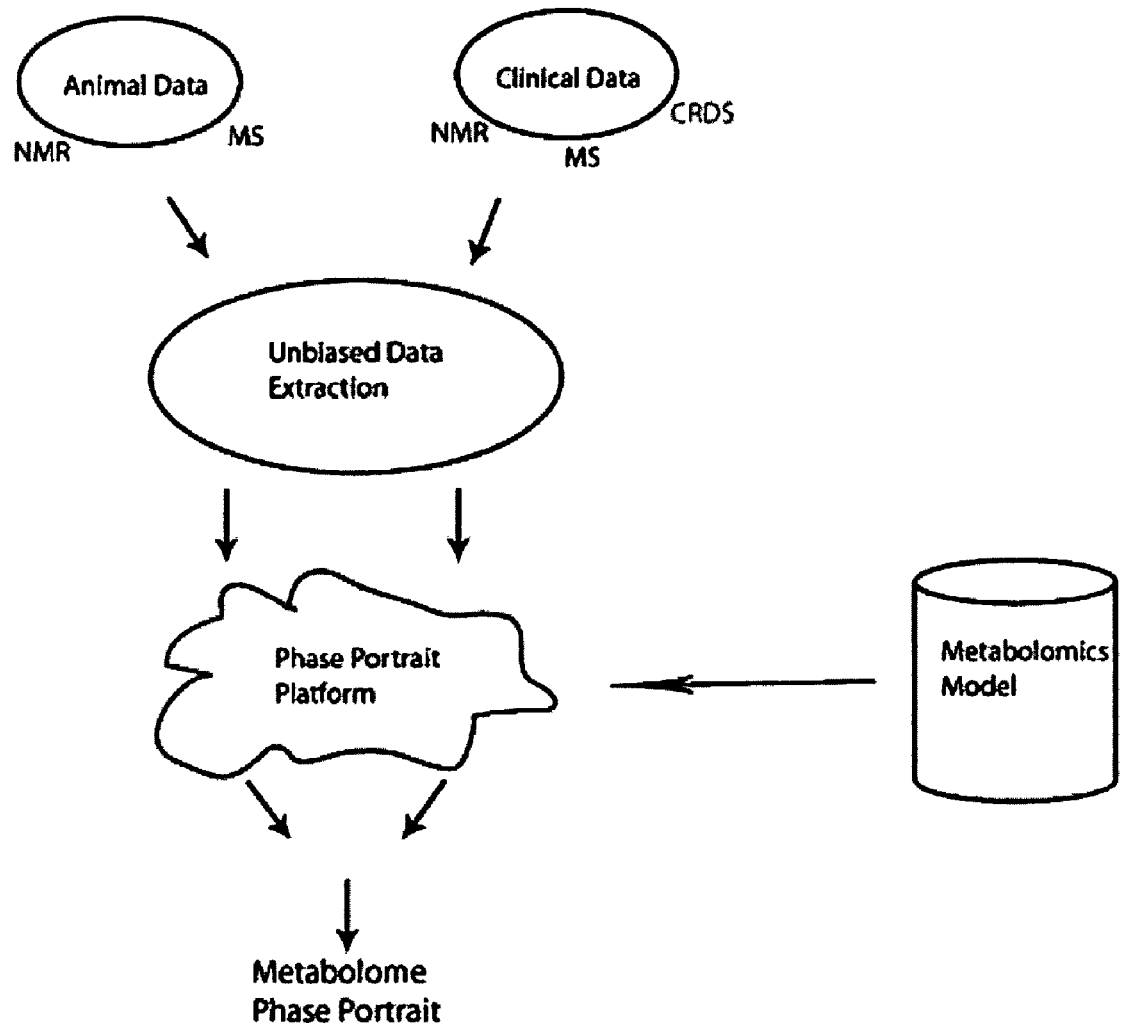
FIG. 15 illustrates use of animal and clinical data in combination with metabolomics models from each species to form a single standard metabolome phase portrait. A standard metabolome phase portrait for a disease state is useful in assays and kits for diagnosing a disease state by measuring biomarker levels from a biological sample.
Figure 16:
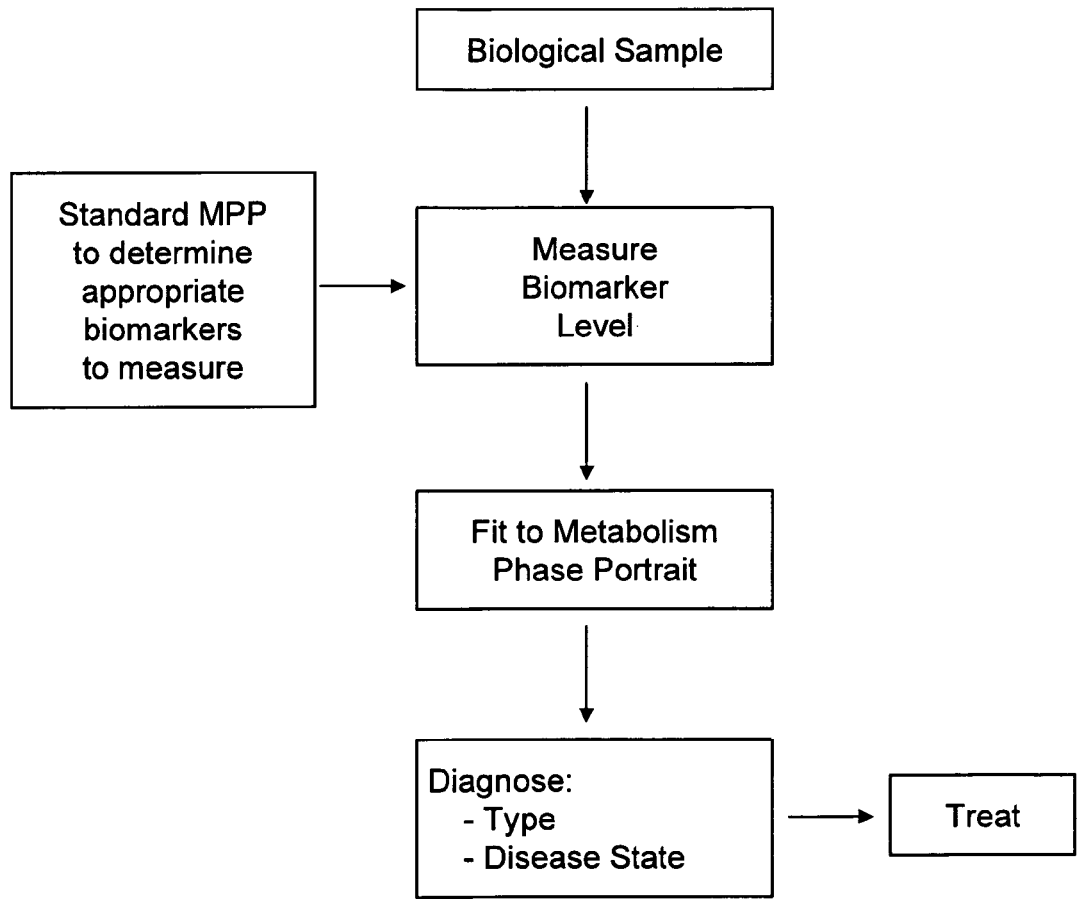
FIG. 16 is a flow-diagram illustrating an embodiment of the invention wherein the standard metabolome phase portrait ("MPP"), such as one developed as summarized in FIGS. 14 and 15, is used to determine the appropriate biomarkers to measure within a biological sample. The biomarker pattern is compared or fit to the standard MPP to diagnose whether a disease is present, the type of disease (including such as bacterial or viral), and the disease state (e.g., progression, whether onset or toward recovery).

Normal phenotypic and environmental variations of metabolite profiles, which are usually referred to as noise, pose challenging obstacles to the identification of patterns. In the case of metabolites in biochemical pathways, the measured signals are the average state of reactants, and disturbance would arise as a consequence of the fluctuations around that average value. In this context, the disturbing effect of these fluctuations is reflected as "noise". This is distinct from large fluctuations in the system parameters that have very short characteristic times compared with those of other processes. To deconvolve noise from phenotypic variations and construct a model of disease progression, the phase portrait approach transforms the data to a statistical space that reports on the "generic" or average metabolite concentration trajectory of a healthy vs. affected (perturbed) system within a fluctuation envelope that characterizes natural variations (see FIGS. 3 and 15).

Inflammatory response is a widely conserved (*Drosophila melanogaster* to *Homo sapiens*) host defense mechanism designed to protect the body from invading pathogens. Tissue damage or invasion of a foreign pathogen initiates a complex cascade of events that defines the acute inflammatory response. Tissue macrophages are activated by cell surface pattern recognition receptors (Toll family receptors) that encounter an invading pathogen. Signaling via NF-κB and AP-1 pathways causes transcription and production of cytokines tumor necrosis factor (TNF), interleukin (IL)-1 and IL-6 and enzymes, e.g. inducible nitric oxide synthase (iNOs) and cyclooxygenase-2 (COX-2), that produce mediators of inflammation. TNF can appear in serum 20 minutes after an inflammatory stimulus. TNF, IL-1 and IL-6 further activate macrophages and neutrophils and act as potent chemotactic factors for additional immune cells.

Stable isotope mass spectrometry reveals that carbon stable isotopes ($^{13}C$ and $^{12}C$) are fractionated during the acute phase inflammation response in a process referred to as the kinetic-isotope effect. During healthy periods, the $^{13}CO_2/^{12}CO_2$ breath ratio contains a higher concentration of $^{12}CO_2$. During acute inflammation, however, the body becomes catabolic, i.e. breaks down stored muscle tissue into its primary constituents, amino acids. These amino acids are now both an energy fuel and source of acute phase proteins. Lighter amino acids are used as fuel, whereas the heavier amino acids are used for the synthesis of acute-phase proteins. Hence, the delta value of the breath becomes more negative. See Hatch et al., BBRC 1995 212:719; U.S. Pat. No. 5,912,178.

Figure 4A:
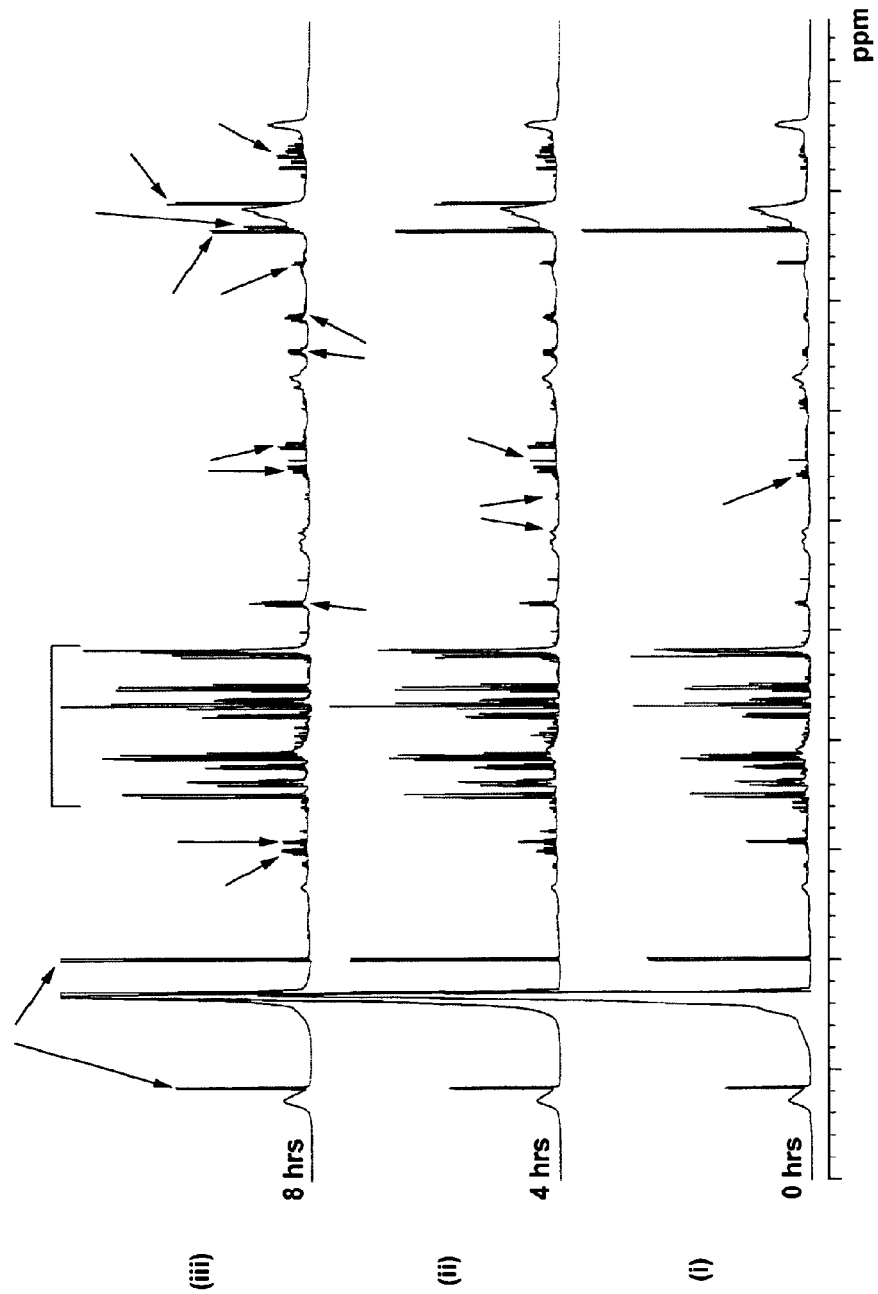
FIG. 4 is the NMR data of FIG. 2 wherein the methodology summarized in FIG. 3 has identified regions of interest that are changing with time. These regions are identified with arrows. The peaks associated with each of the arrows belong to molecules changing in the plasma after injection with endotoxin (e.g., LPS).
FIG. 4B is a close-up view of a region in FIG. 4A to more clearly show particular peak changes with time (0, 4 and 8 hours).
Figure 4B:
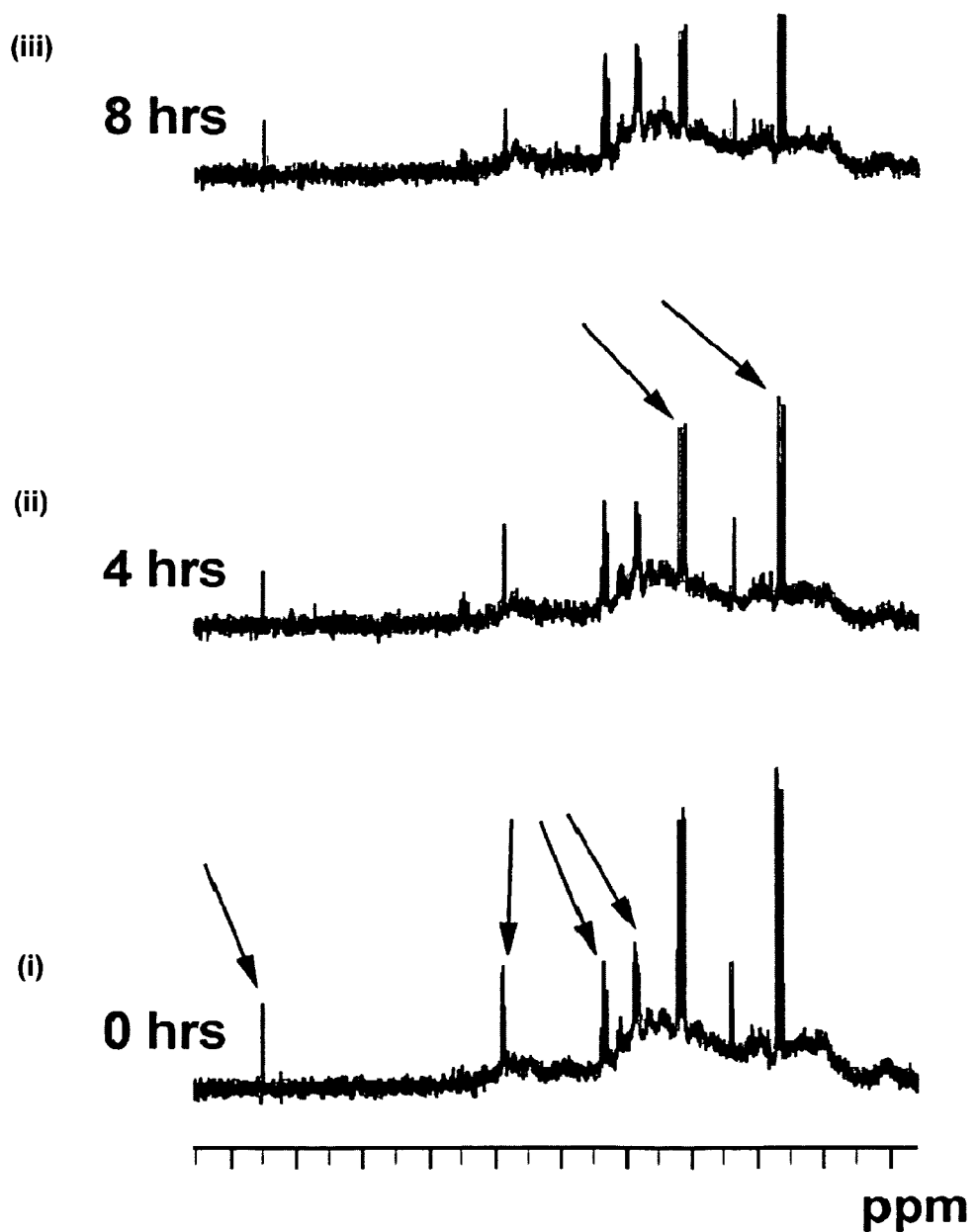
Figure 5:
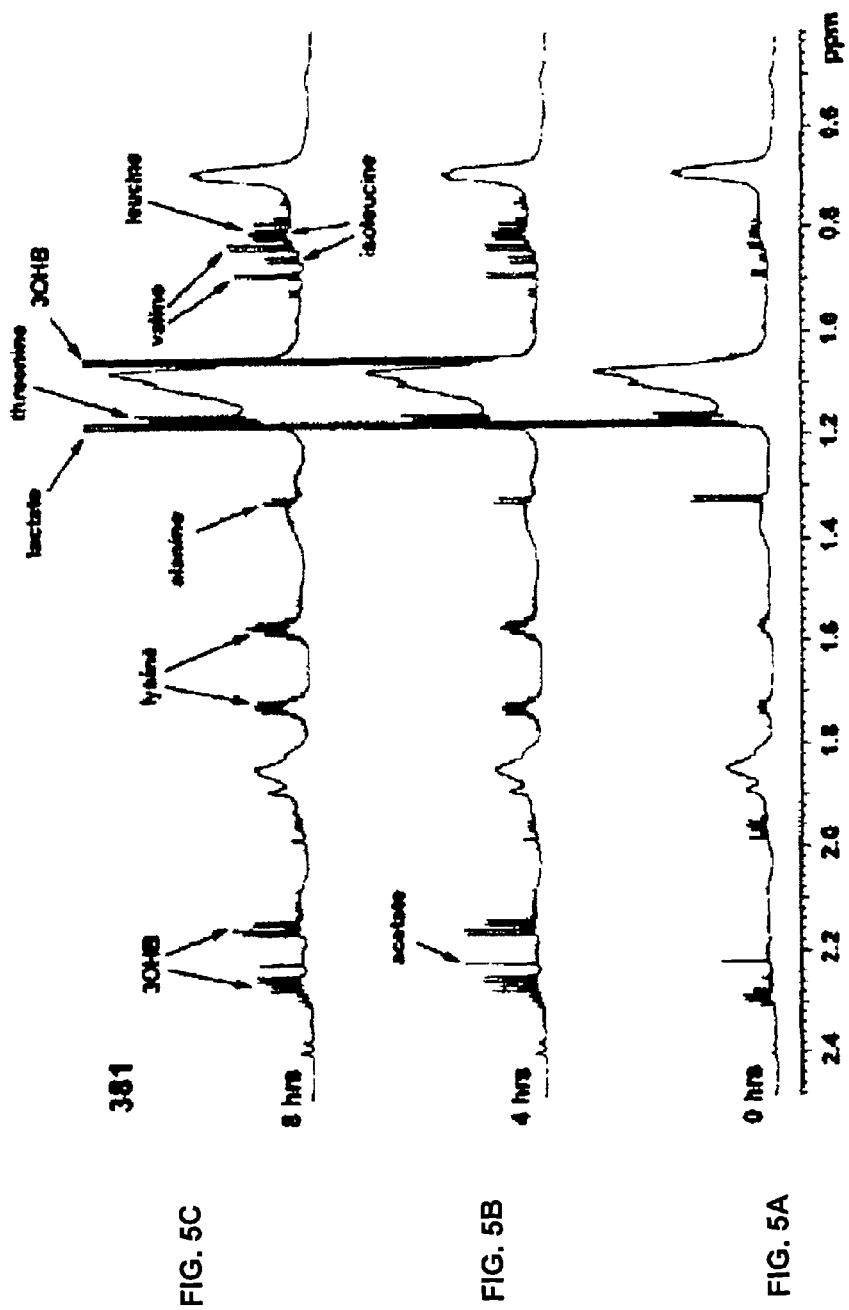
FIG. 5 is a 1-D $^1$H NMR spectra showing changes in specific biomarkers from blood plasma with progression of disease state. The bottom plot (A) is for immediately preceding endotoxin administration (0 hrs) and is a "normal" baseline; the middle plot (B) is 4 hours after endotoxin administration; the top plot (C) is 8 hours after endotoxin administration. Peaks corresponding to biomarkers of interest are labeled accordingly. The experiment is recorded at 800 MHz on a Varian Inova spectrometer equipped with a cryogenic probe.
Figure 6:
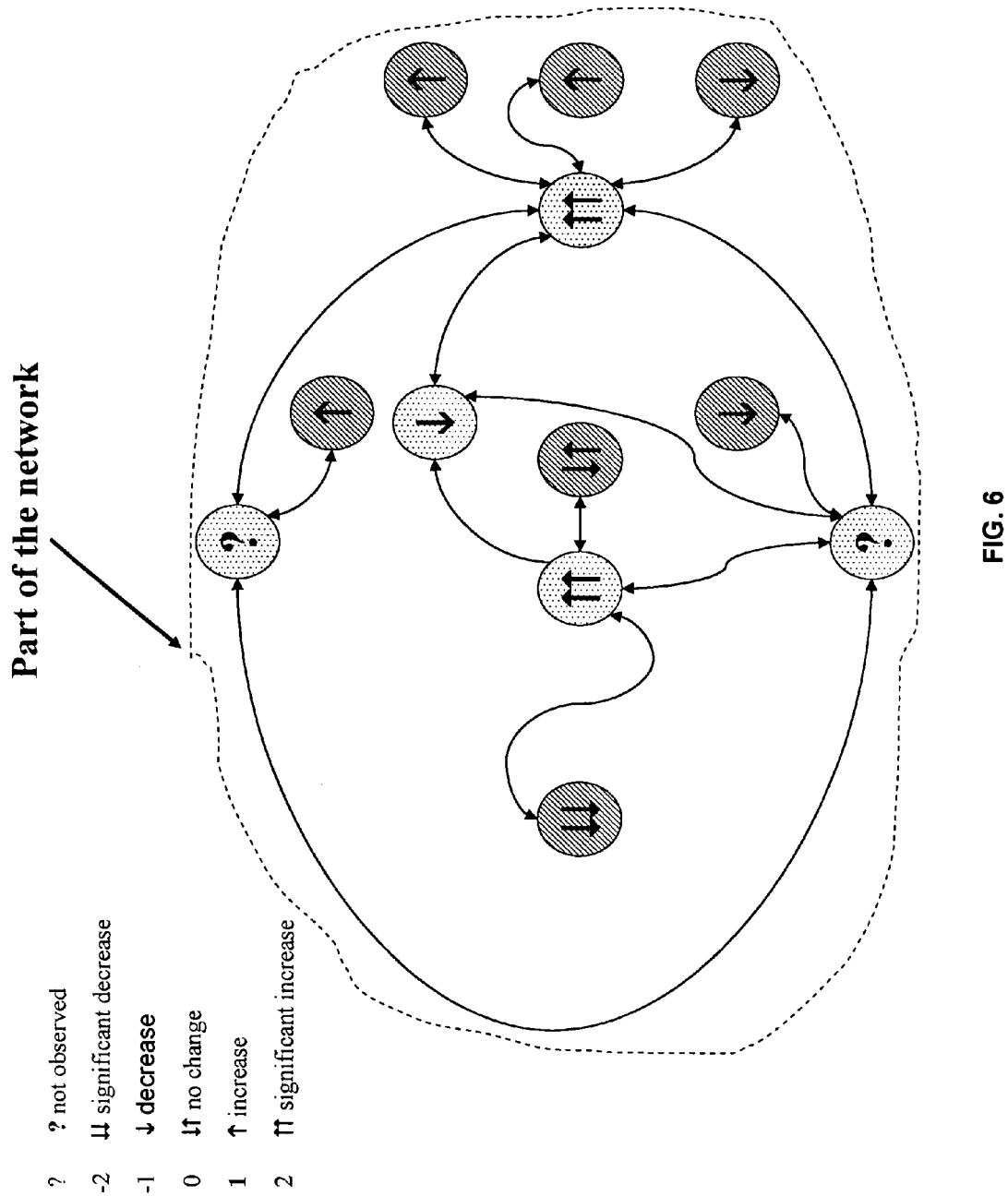
FIG. 6 is an illustration of the data mapping stage model containing 12 biomarkers and associated changes in each of the biomarkers with disease progression. For each node, corresponding to a putative biomarker, one of six states is identified as summarized in the legend.
Figure 7:
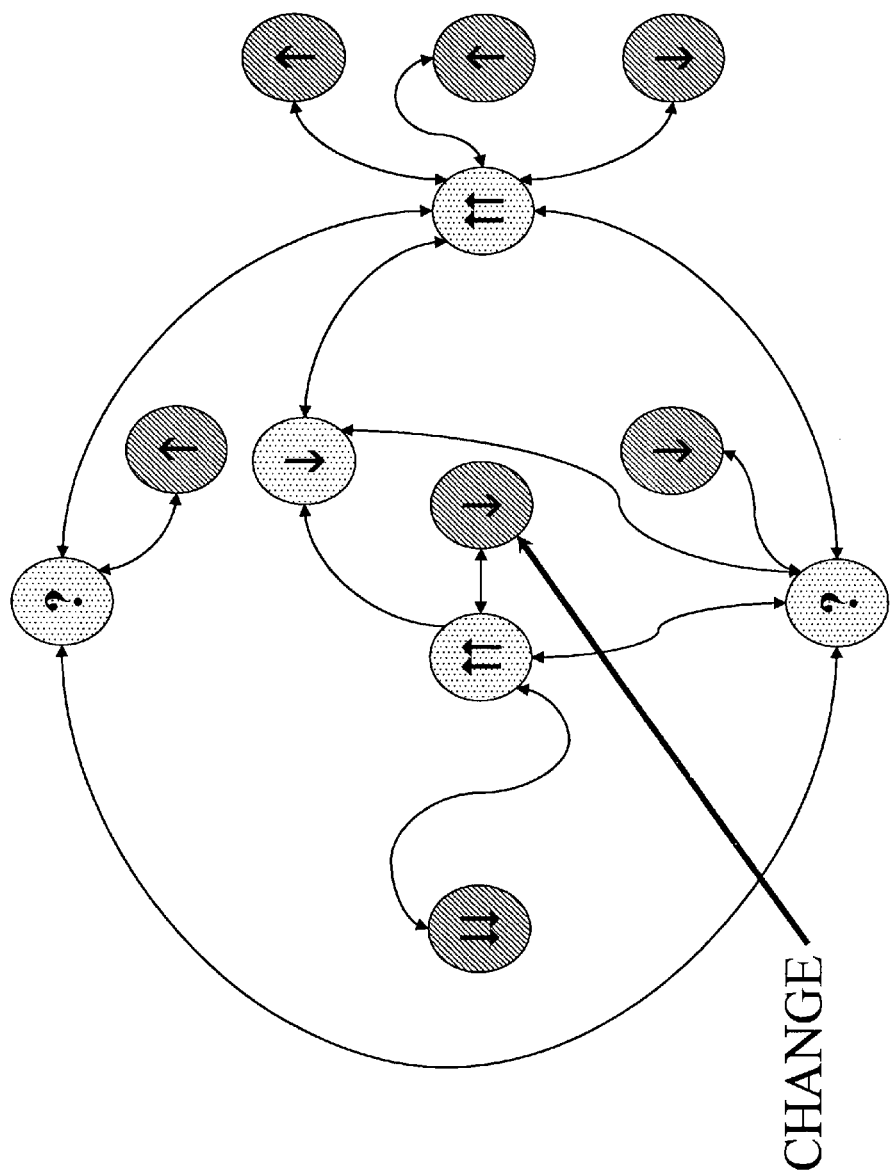
FIG. 7 illustrates the significance of detecting and analyzing the "no-change" node in FIG. 6 because for another sample at a different time point (e.g., different disease progression state) the node labeled "change" has changed from a "no-change" state to a "decrease." In this manner, disease progression is determined by stacking models in a time-dependent fashion.
Figure 8:
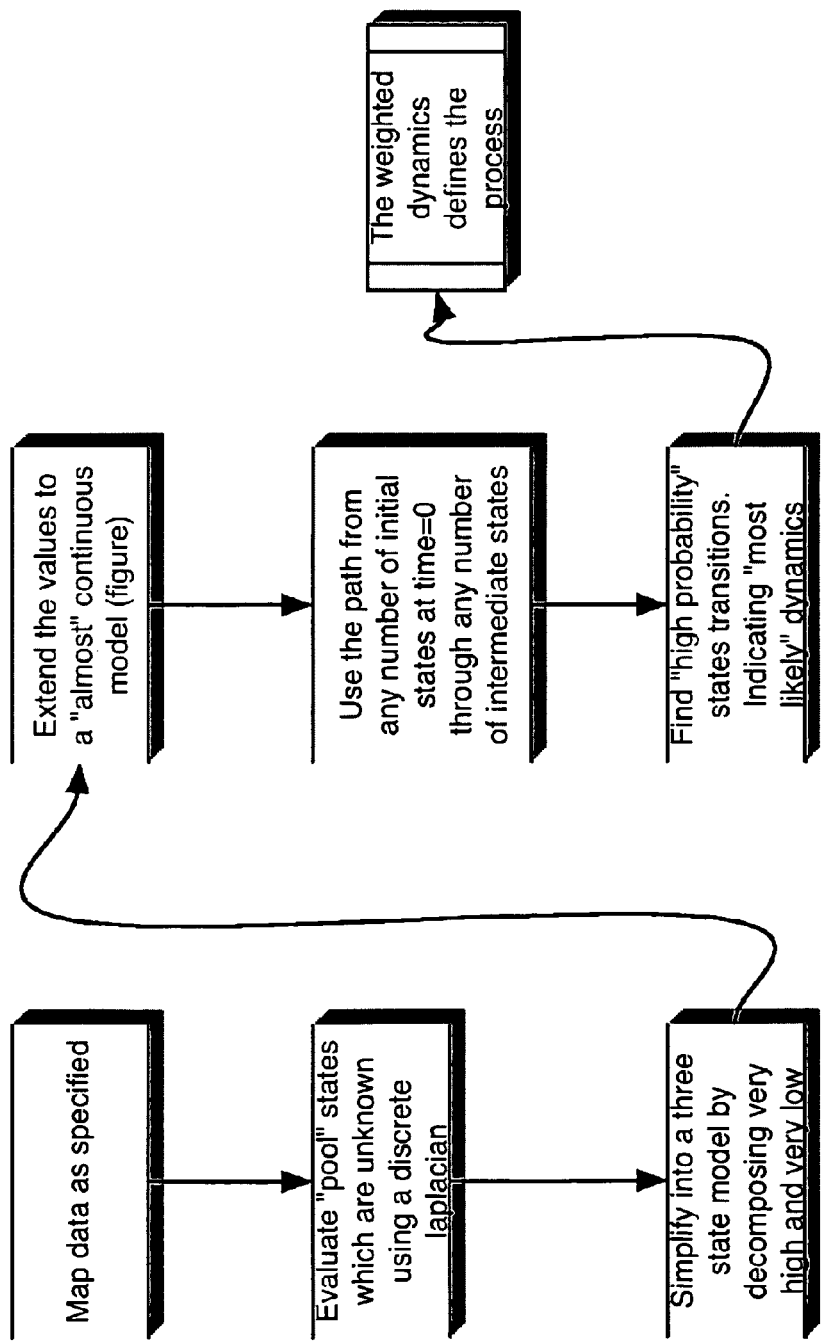
FIG. 8 summarizes the methodology for using changes in observed biomarker levels to reduce the total number of parameters in the metabolic network necessary to reliably model the network.
Figure 9:
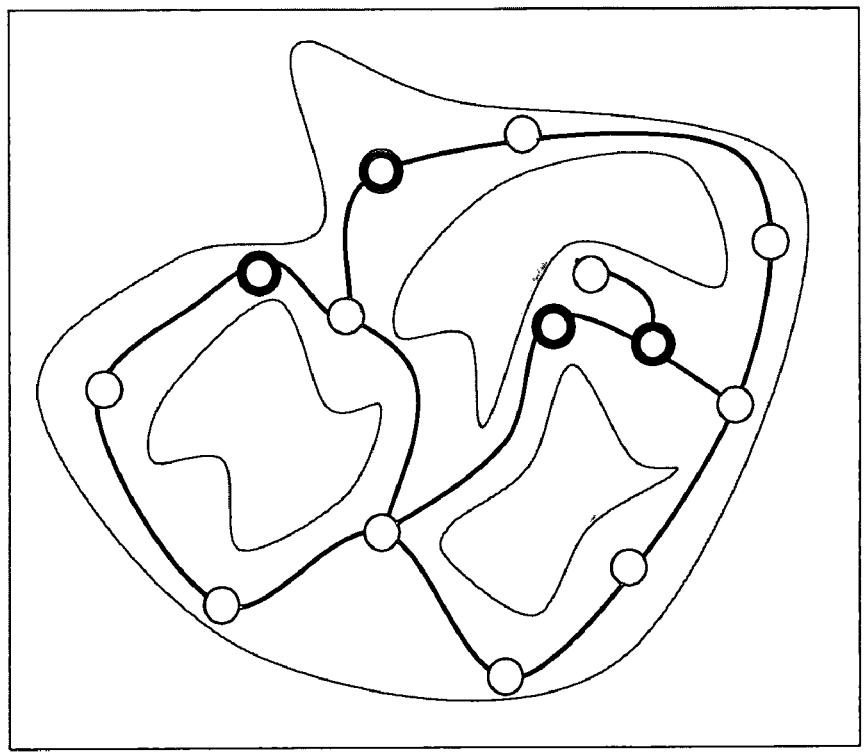
FIG. 9 is a pictorial overview of the process summarized in FIG. 8. Probabilistic metabolome flux analysis reveals important dynamics of metabolic changes. The figure depicts a snapshot (at a single time point) for the dynamics of 13 metabolites. The nodes have one of three states: constant (circles with thin border); increasing (thick border); and decreasing (gray-filled). The three "irregular" shapes within the map indicate the probability of change with positive change probability shown in lighter colors and negative change shown in darker shades.
Figure 10:
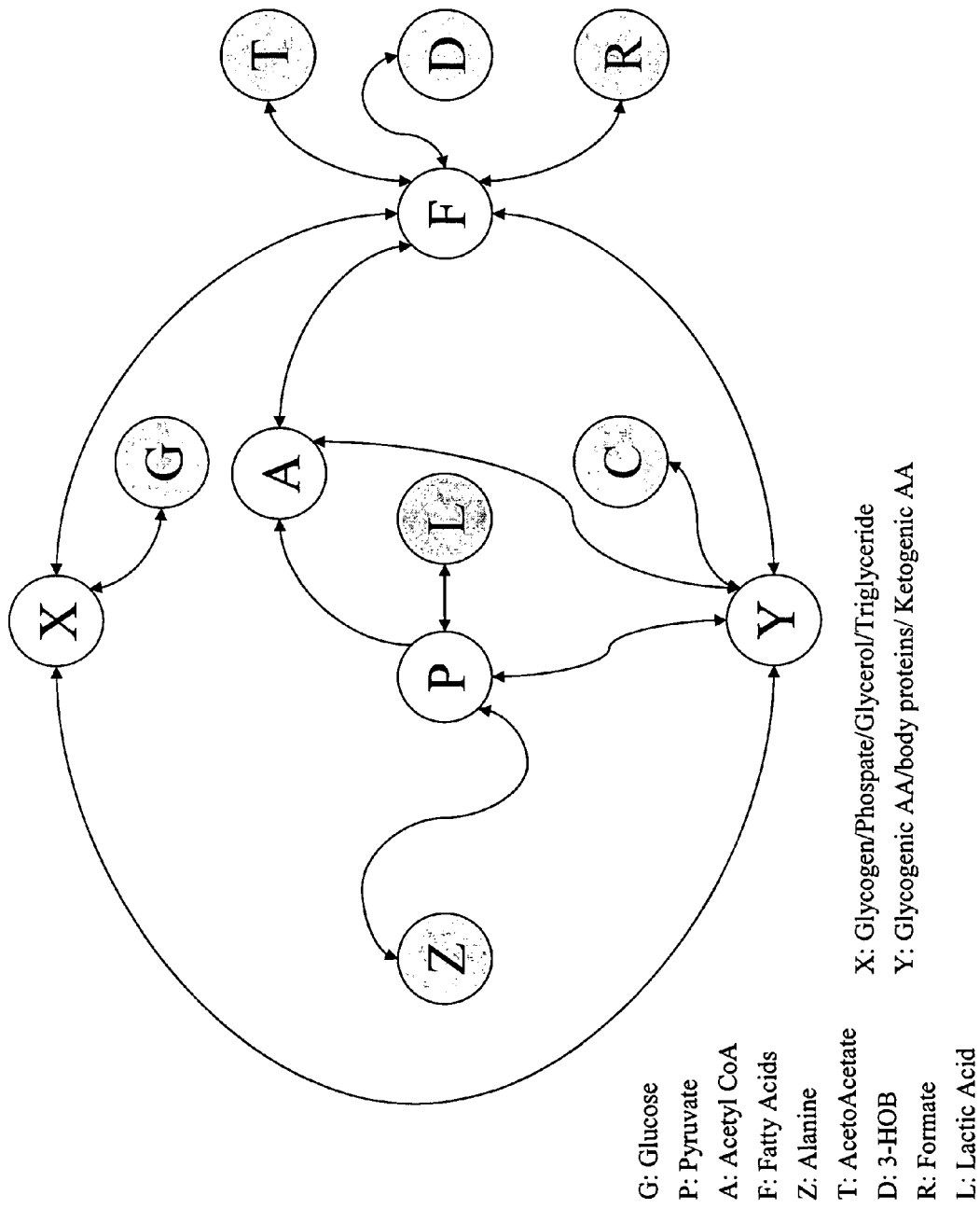
FIG. 10 shows the reduced model obtained from a biological sample from a cachexia-induced subject.
Figure 11:
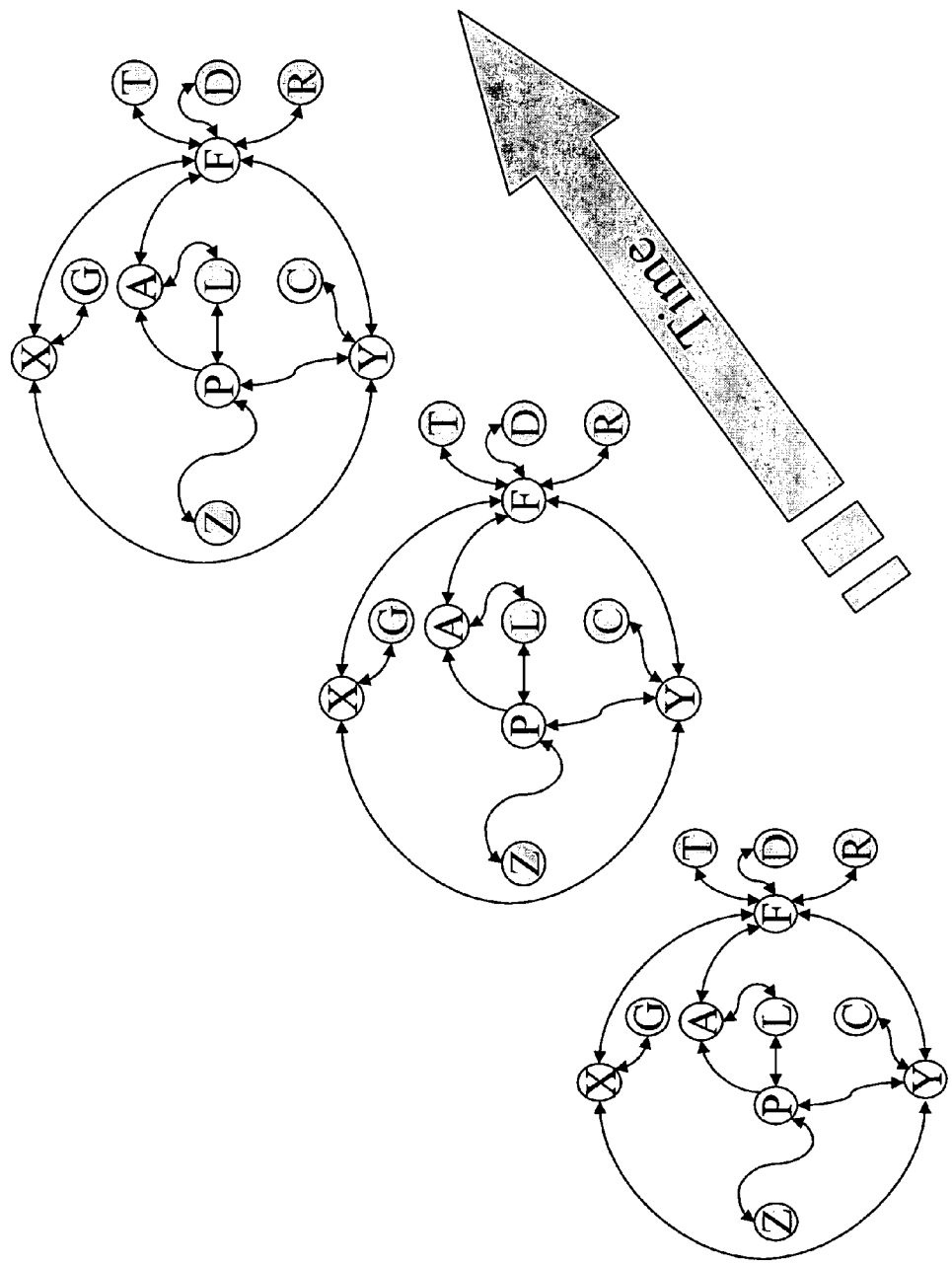
FIG. 11 illustrates that the reduced model of FIG. 10 forms a template for assessing biomarker patterns or profile as a function of time. The template is useful for providing baseline information on a disease state and is used to diagnose disease state for subsequent biological samples. Repeated measurements of these biomarkers as a function of disease state progression (labeled as the time axis) generates a standard metabolome phase portrait for the disease state. The standard metabolome phase portrait is used to assist in diagnosing disease state when testing biological samples.
Figure 12:
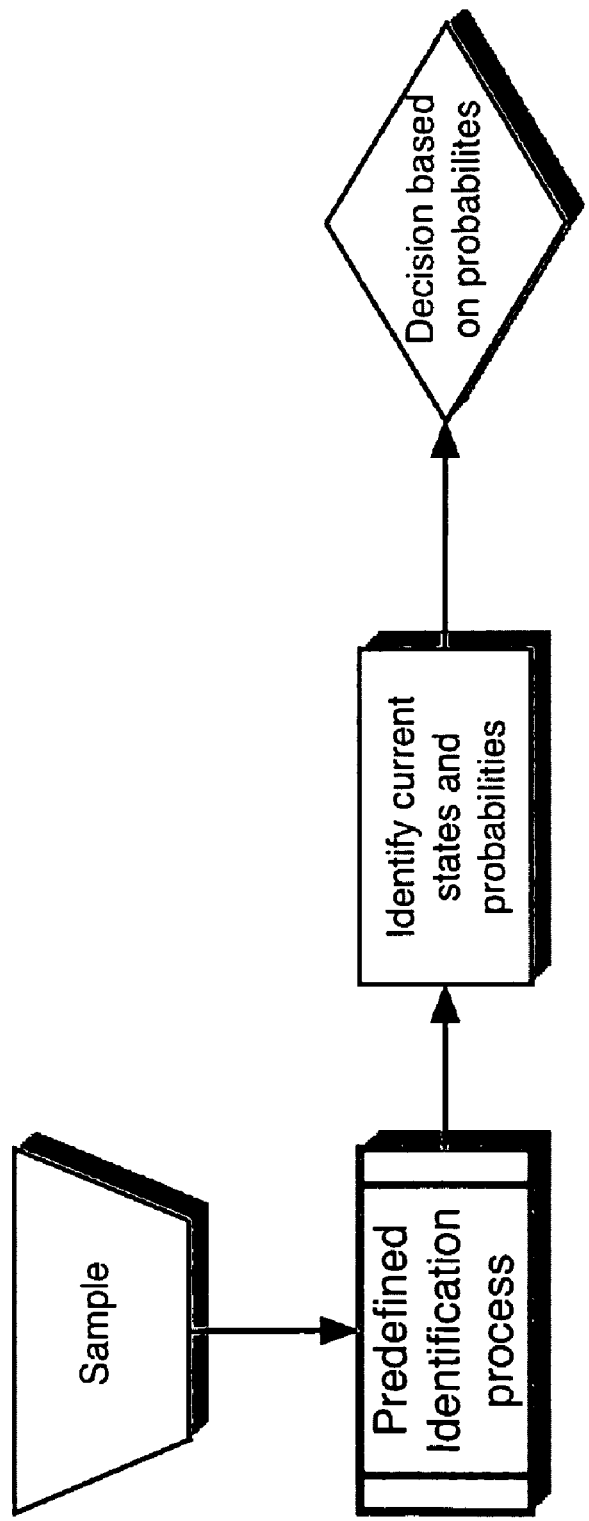
FIG. 12 is an overall flowchart for identifying a condition. Patterns derived from a sample are mapped and a description of the continuous shape changes of the pattern obtained to identify the probability of the current state.
Figure 13A:
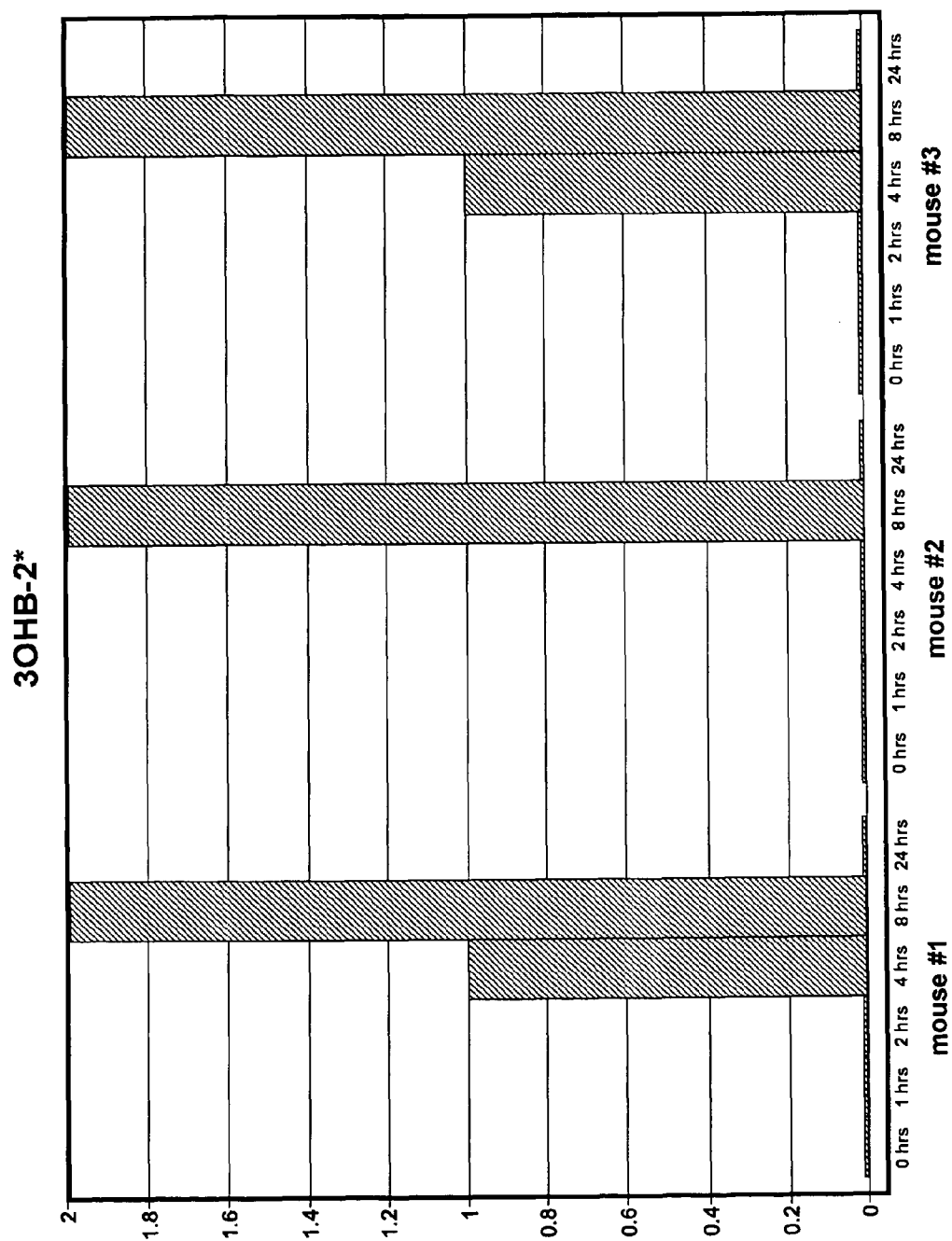
FIG. 13 is a graph of biomarker changes as a function of time in mice injected with LPS (data provided in Table 1). The y-axis uses a scale as defined in FIG. 6 (−2 significant decrease; −1 decrease; 0 no change; 1 increase; 2 significant increase) for a given biomarker. Each of the plots in A-H represents an individual biomarker (3-OHB-2, Acetoacetate, Ala-CH3, α-glucose, citrate, lactate-CH3, formate, glucose-Ca, respectively) for three individual mice as a function of time (0-24 h) post-injection. Common biomarkers and their changes are conserved across species. I is a summary of the 8 biomarkers change with time for an individual mouse.
Figure 13B:
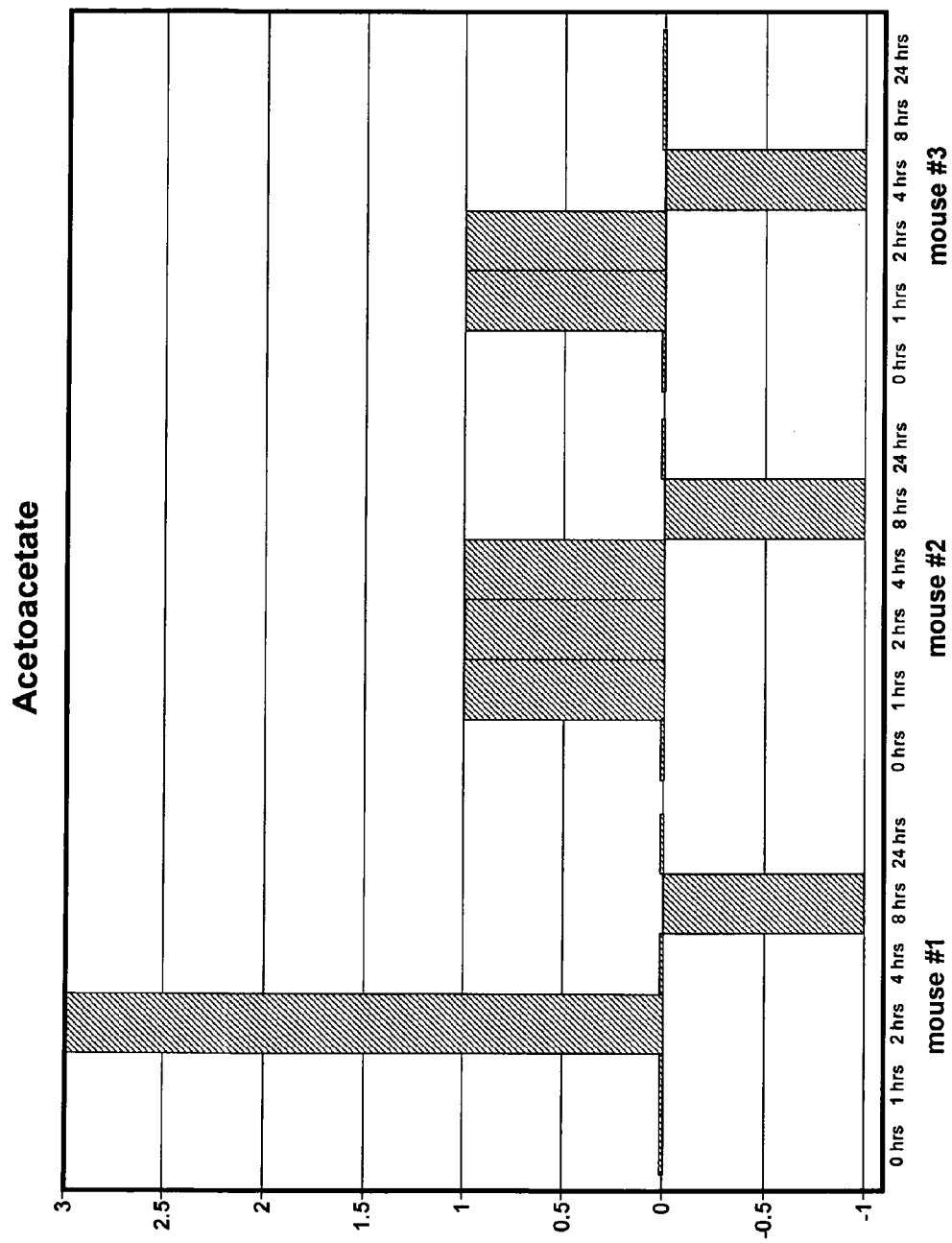
Figure 13C:
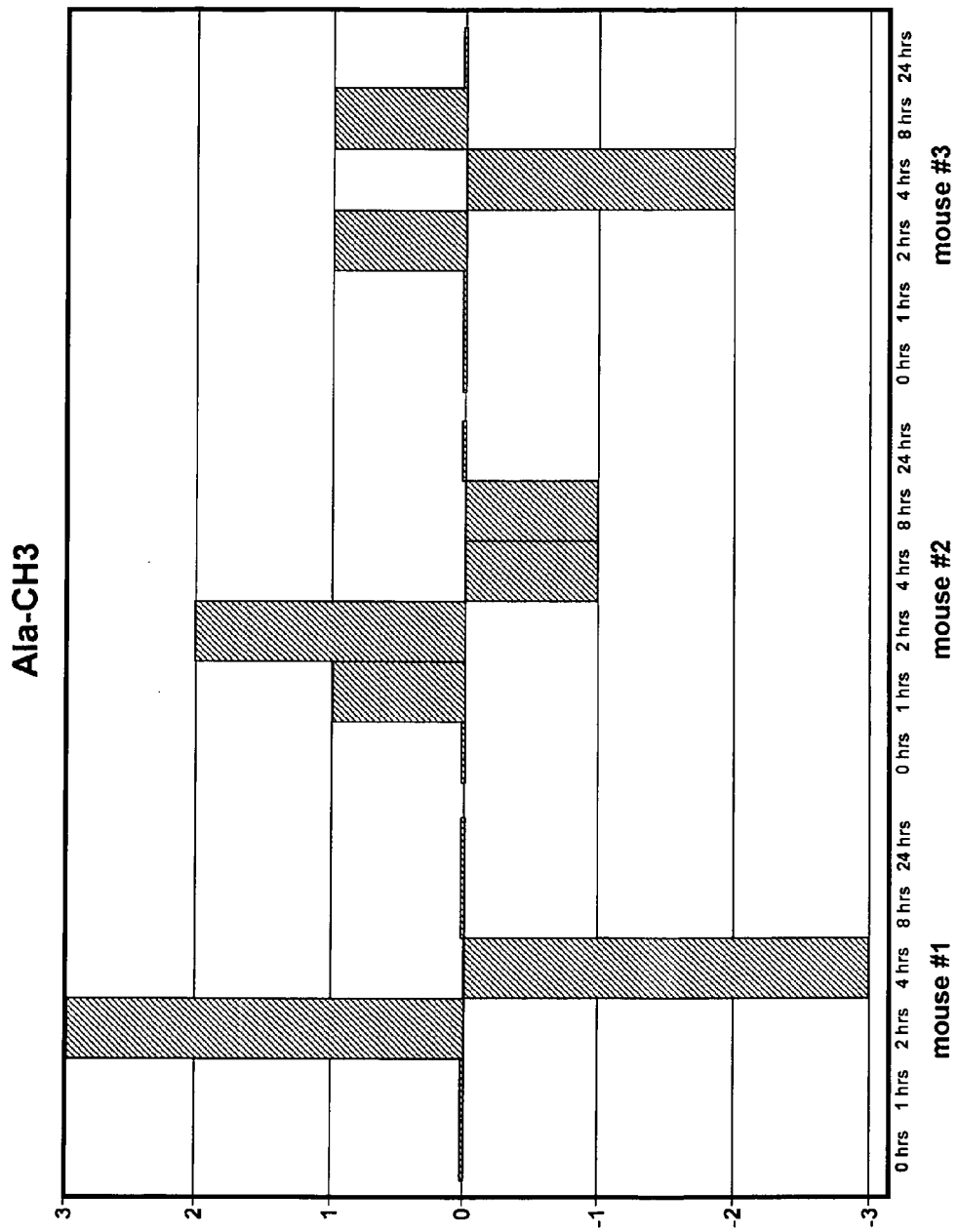
Figure 13D:
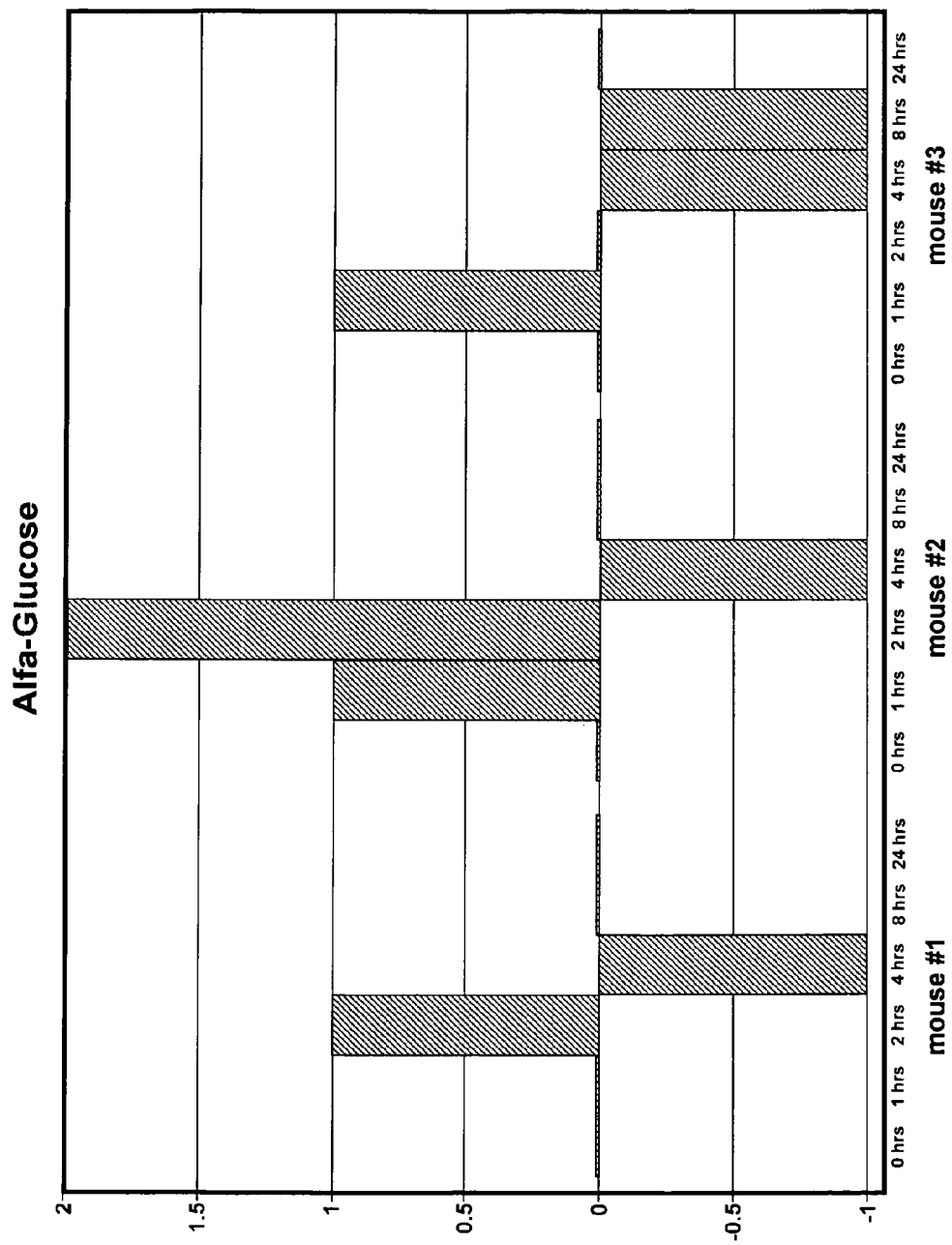
Figure 13E:
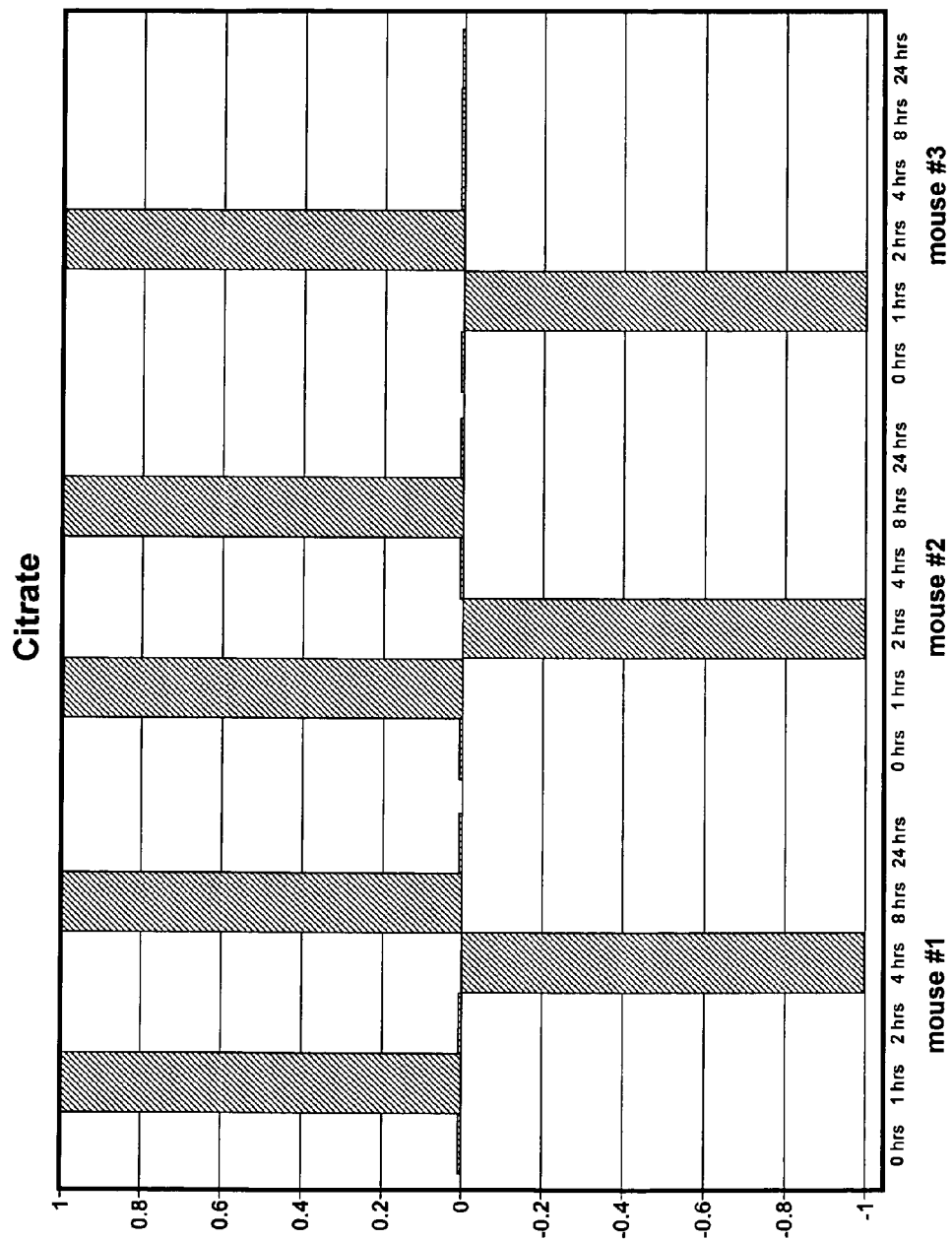
Figure 13F:
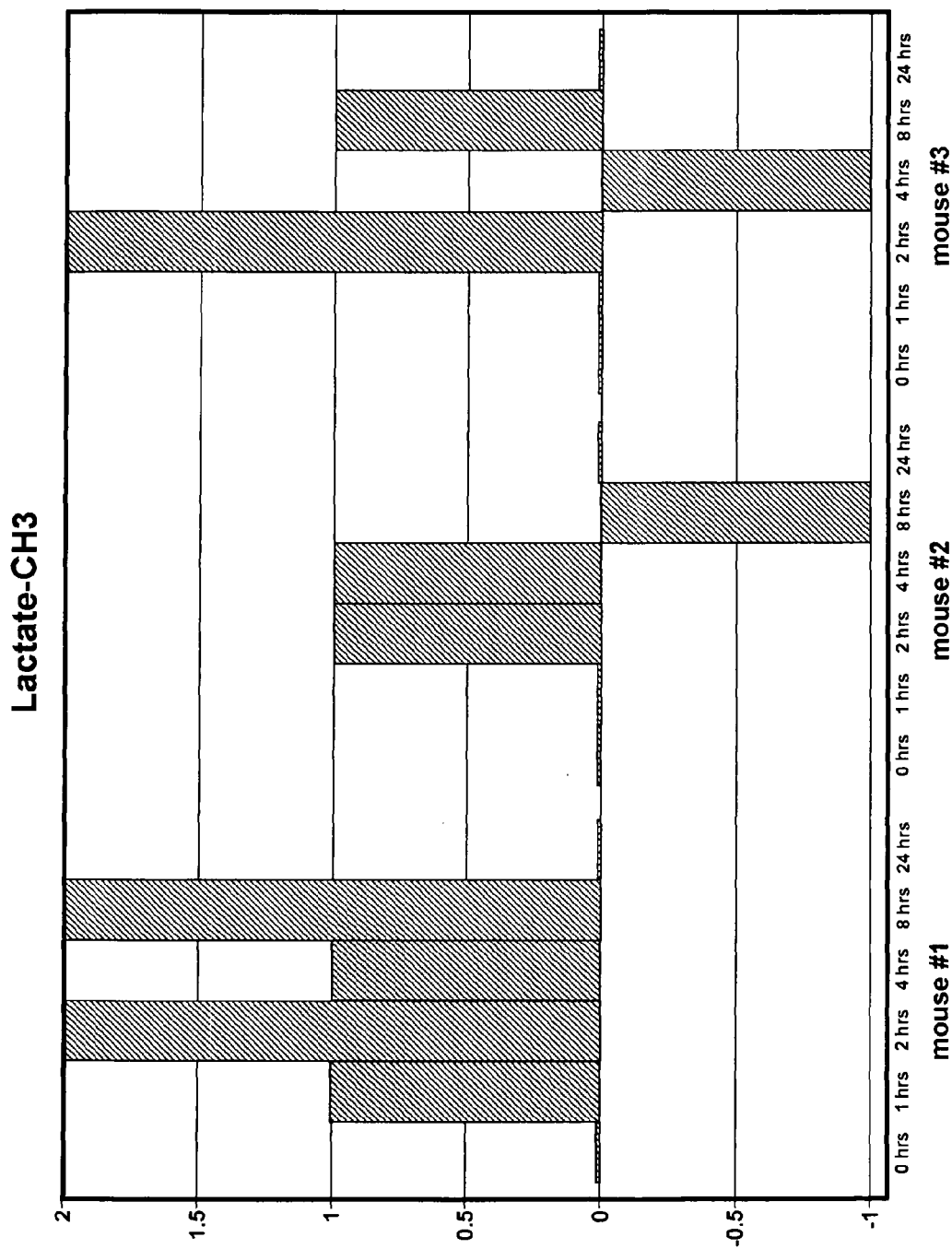
Figure 13G:
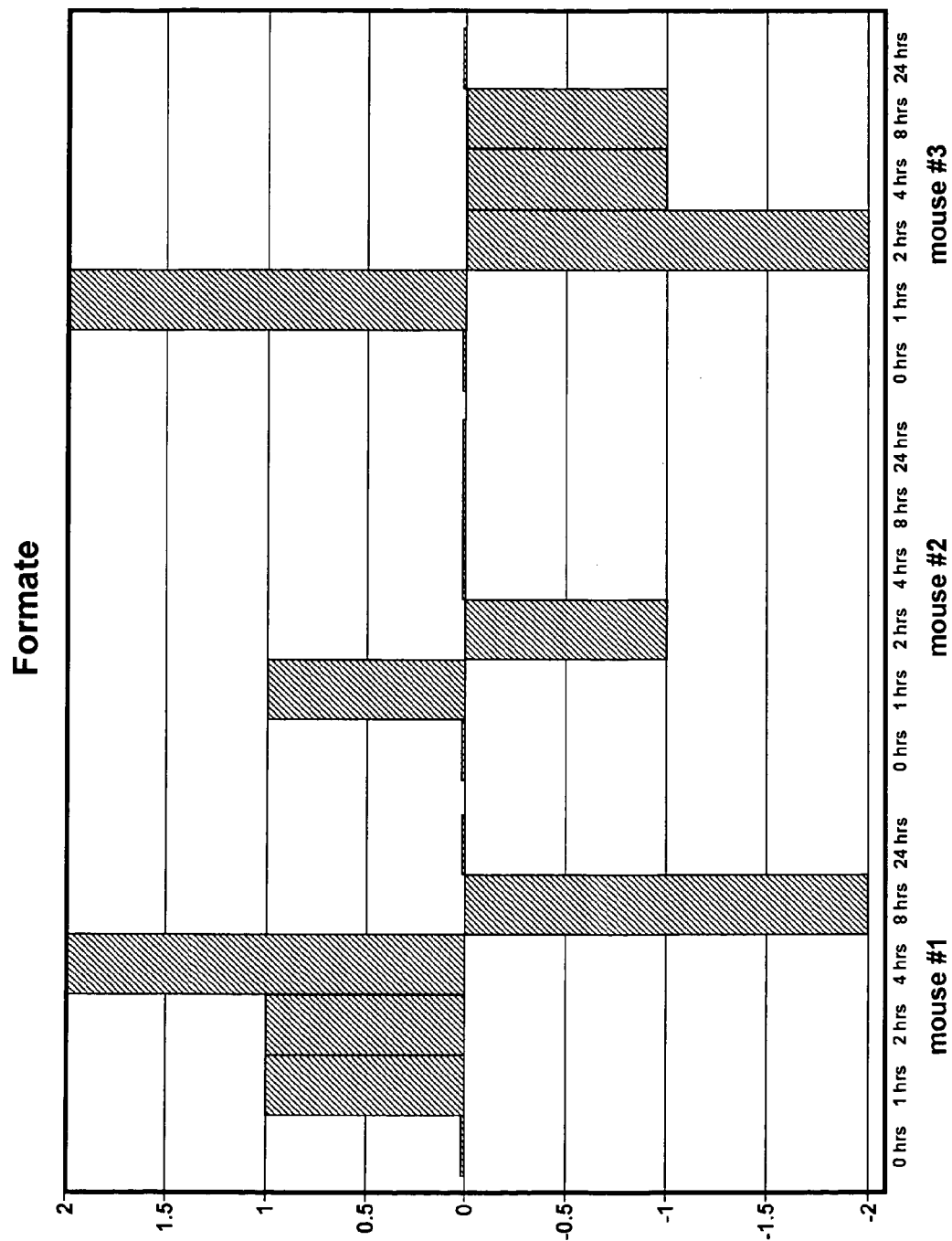
Figure 13H:
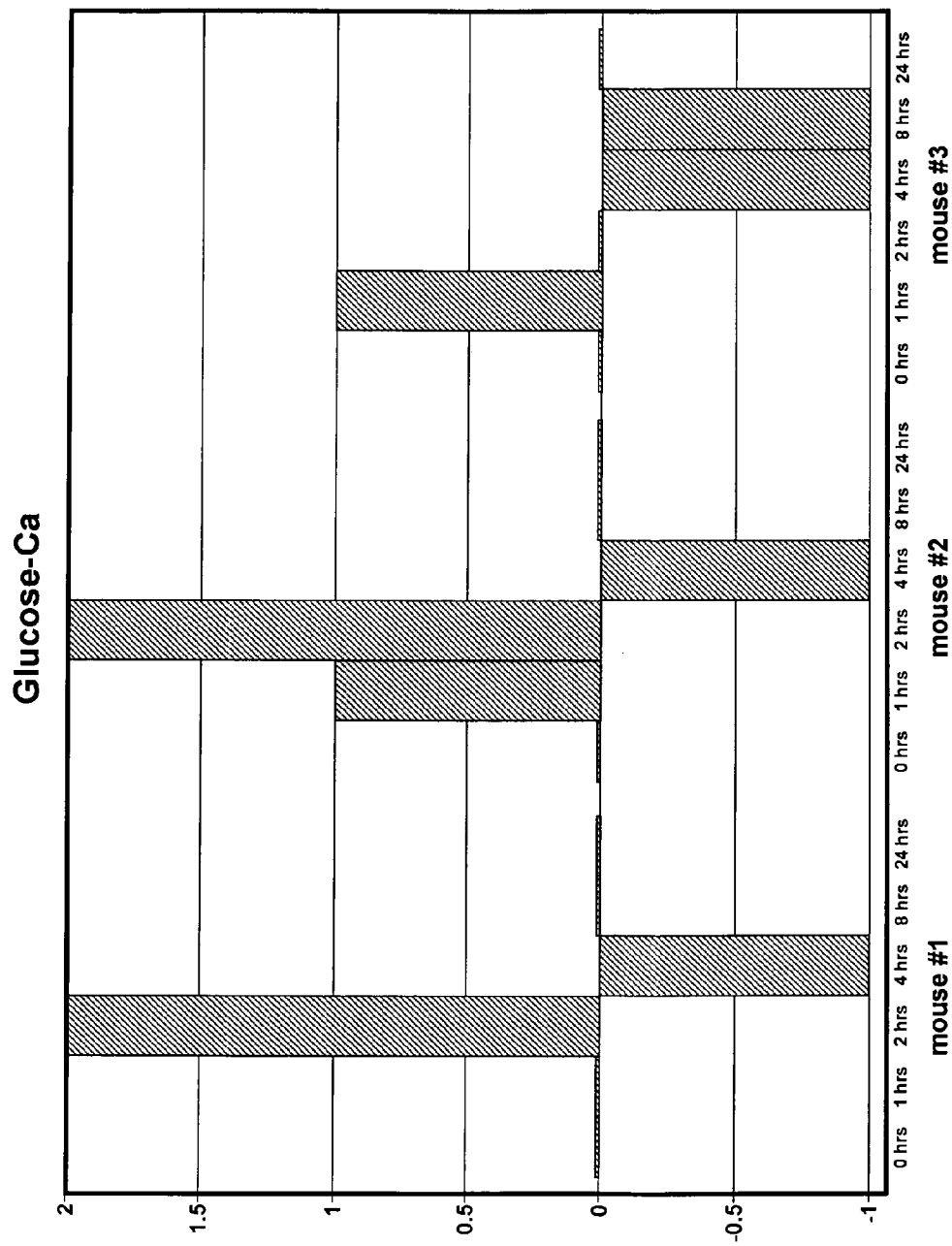
Figure 13I:
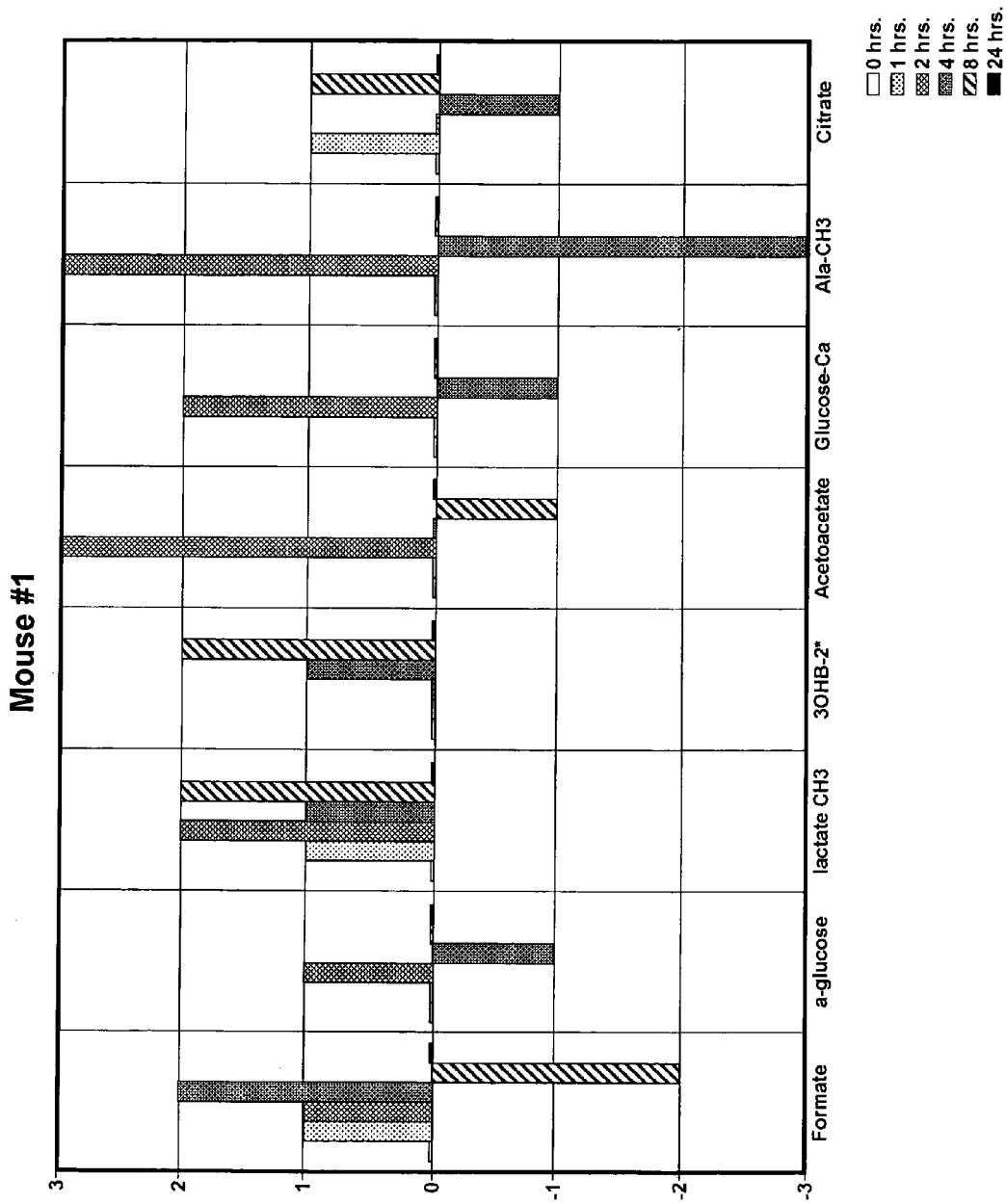

The trajectory of biomarkers in chickens and mice following lipopolysaccharide (LPS) injection which generates acute inflammation biomarkers, is used to further develop the phase portrait model for cachexia disease state. Serum samples that form the basis for these acute phase discoveries are analyzed using NMR spectroscopy (FIG. 4). A suite of 14 biomarkers and their trajectories are identified during an inflammatory response. The methodology developed herein facilitates a description of the trajectory and the pattern of responses to infection reliably. In order to extract the data in a reliable and robust manner, we use a probabilistic approach and automated fast NMR data collection [Eghbalnia et al. J Am Chem Soc 2005 127:12528] and analysis [Eghbalnia et al. J Biol NMR 2005 32:219; Eghbalnia et al. J Biol NMR 2005 32:71]. The probabilistic methods assist in identifying spectral features of high-resolution 1D $^1H$ NMR spectra and specifying regions of interest and probability of significance. Once such regions are located (FIG. 4 arrows), we rapidly identify the metabolites changing in response to the LPS treatment directly from the $^1H$ 1D NMR spectra or by analyzing the relevant regions in 2D NMR spectra such as $^1H$—$^1H$ TOCSY and $^1H$—$^{13}C$ HSQC. These time-costly experiments are performed when needed to reduce peak overlap in crowded regions, to enhance the information content and further confirm calibrations and biomarker identification. Of the thousands of small molecules present in the samples that are detected by NMR, the approach herein identifies 14 biomarkers that changed in response to the LPS treatment. The plasma concentration of some of these biomarkers increases or decreases over time, while others initially increase then decrease or vice versa. Importantly the biomarkers that are identified vary independently over time. Thus the biomarkers form the basis of an essentially orthogonal n-dimensional space (where n=the number of independently varying biomarkers) that is the core of the metabolome phase portrait. The phase portrait methodology incorporates the observed metabolites into a dynamic probabilistic network of interactions to generate regulatory models that are checked for consistency with our knowledge of the systems (FIG. 9). The role of probabilistic analysis in this case, as in the case of NMR, narrows the search and suggests approaches with a high probability of success. This general approach provides a powerful means for analyzing and modeling multiple data sets from other experimental methods such as mass spectrometry to better understand network structures.

An aspect of the biomarker results is the consistency of the findings with known metabolic pathways and processes involved in inflammation. The features of the NMR spectral information discovered using the unbiased probabilistic approach are consistent with previous findings obtained using the stable isotope methodology, thus assuring that the observed patterns are not due to healthy metabolome activity.

Phase Portrait. The phase portrait approach incorporates a probabilistic methodology within the network system parameter identification to give a quantitative account of the dynamics of a metabolic system without requiring any explicit information about the functional form of the rate equations. This approach can overcome some of the challenges outlined above by essentially remaining only probably committed to any model or parameter value. To overcome the computational complexity that often plagues probabilistic approaches, the approach is based on constructing a local statistical model at each point in parameter space, such that each element of the model is either directly experimentally accessible or amenable to a straightforward biochemical interpretation. Then we glue the ensemble of local models, and enforce compatibility conditions in order to obtain a probabilistic exploration of the entire parameter space. The evolution of the points in the statistical manifold yields a "phase portrait". Other probabilistic methods for metabolic system analysis have been proposed [Li & Chan Faseb J 2004 18:746], however, the method described herein differs significantly in both approach and practice. The practical consequence of the differences enables us to work with large and less certain model systems with possibly conflicting experimental data or knowledge-based data. This feature enables the scalability and extendibility of the present approach.

The metabolome phase portrait reveals the metabolic progression of cachexia over the course of disease progression from onset to recovery. Key biomarkers at each stage of the disease are applicable to humans and useful for early diagnosis and development of treatment regimens.

Polycystic ovary syndrome is another disease capable of analysis by the methods of the present invention. PCOS is characterized by infertility due to anovulation, abnormal secretion of androgens and other hormones, and insulin resistance. PCOS is the most common female endocrine disorder, affecting four to seven percent of women in their reproductive years—the syndrome accounts for 75 percent of all anovulations. PCOS has staggering adverse physiological, psychological and financial consequences for women's reproductive health. The "metabolic analysis" method discussed herein permits detection and statistical modeling in changes in a subset of molecules within the body's total pool of metabolites that are reliable, early indicators of PCOS. In particular, control samples are obtained from rhesus monkeys with PCOS, thereby generating a PCOS metabolome phase portrait, by means known in the art such as stable isotopes, NMR, MS, and advanced mathematical computation.

The applicability of the processes disclosed herein for diagnosing disease state in humans is confirmed by examining biomarker profiles in samples obtained from humans in a disease state (see FIGS. 18-21). A similar biomarker trend is observed in human sepsis samples compared to the LPS-induced animal data presented herein, with changes in flux of amino acids and organic acids between control and disease state.

Figure 18:
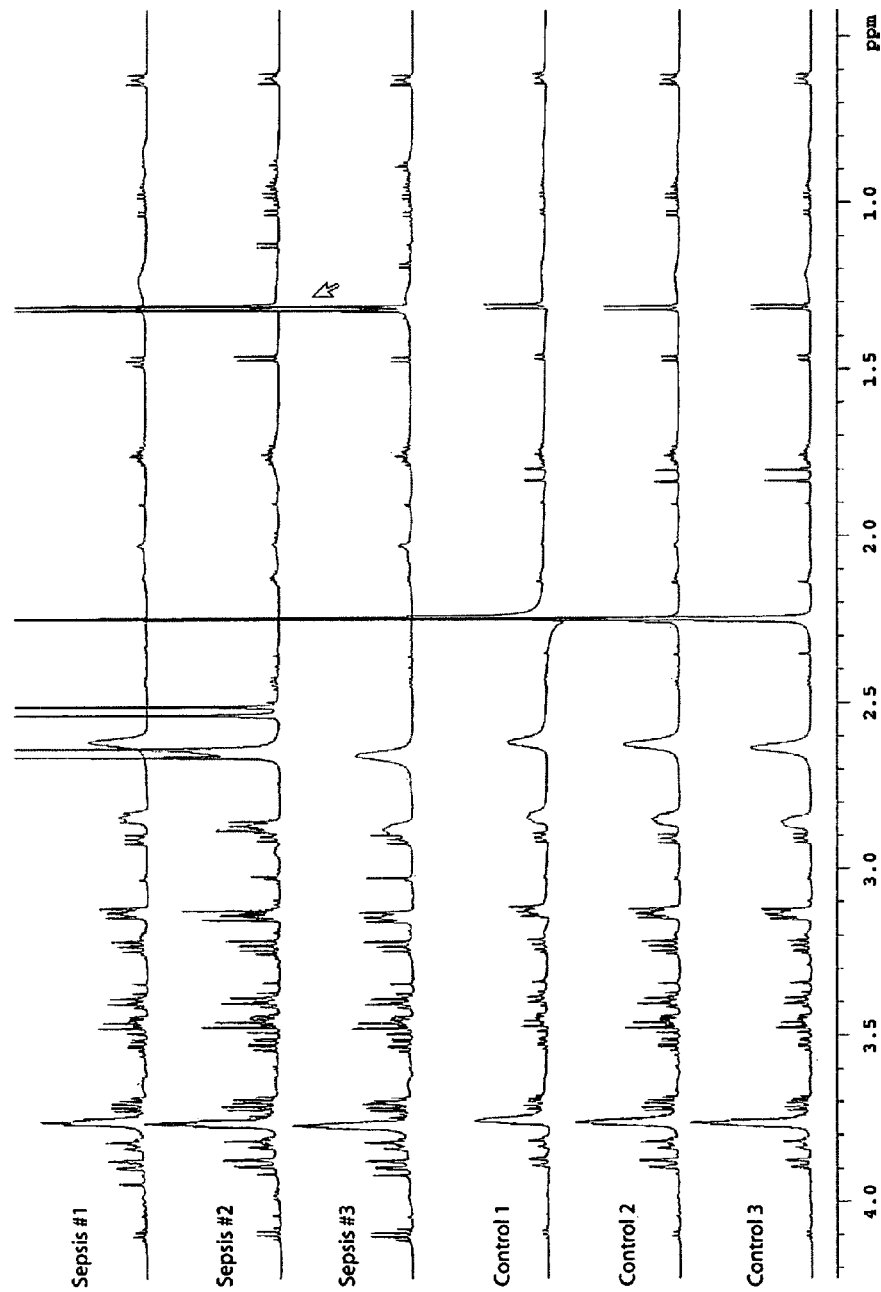
FIG. 18 is a large section NMR spectra of serum samples obtained from human control (bottom three traces) and human sepsis (top three traces) subjects.
Figure 19:
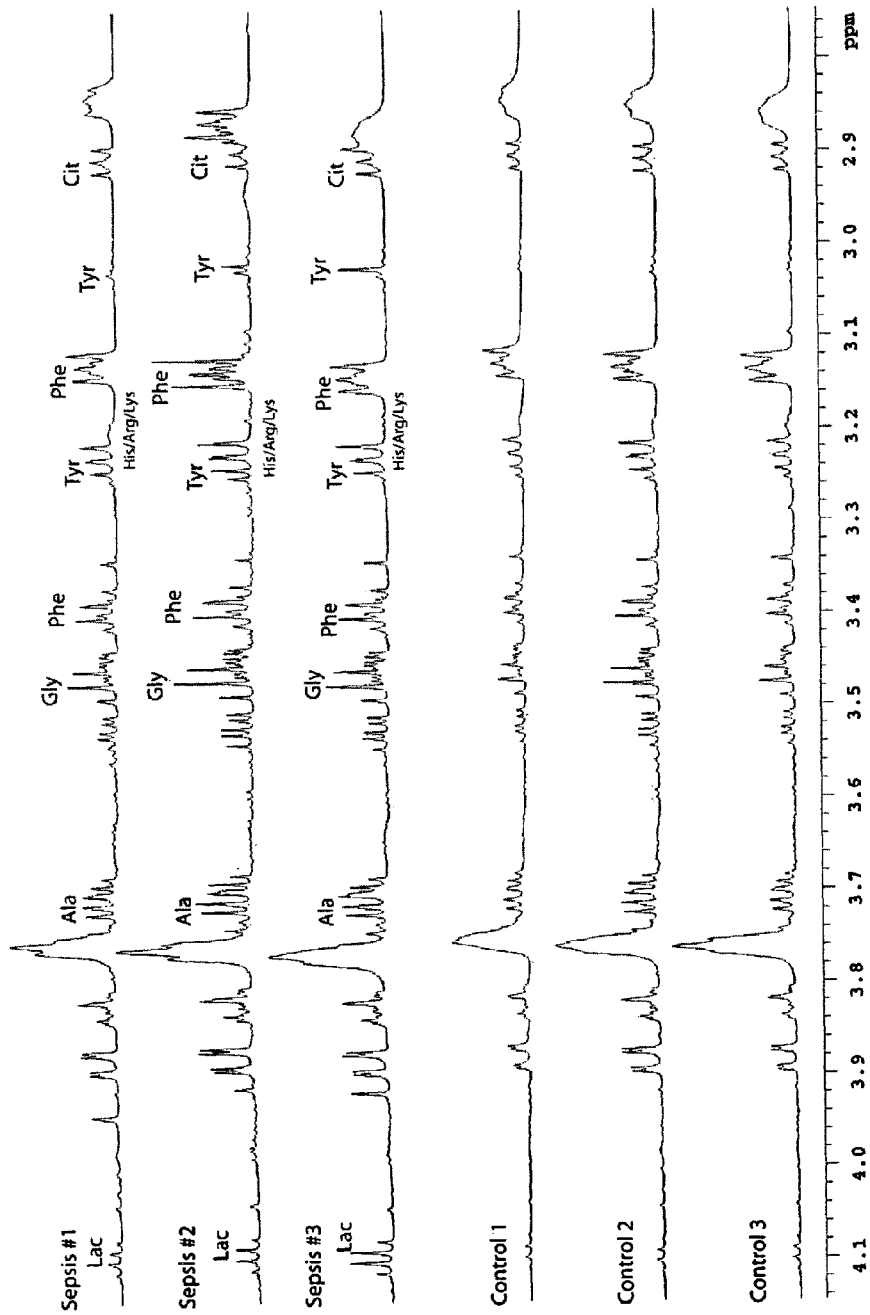
FIG. 19 focuses the NMR traces of FIG. 18 on the aliphatic region. The biomarkers are related to changing peaks are annotated.
Figure 20:
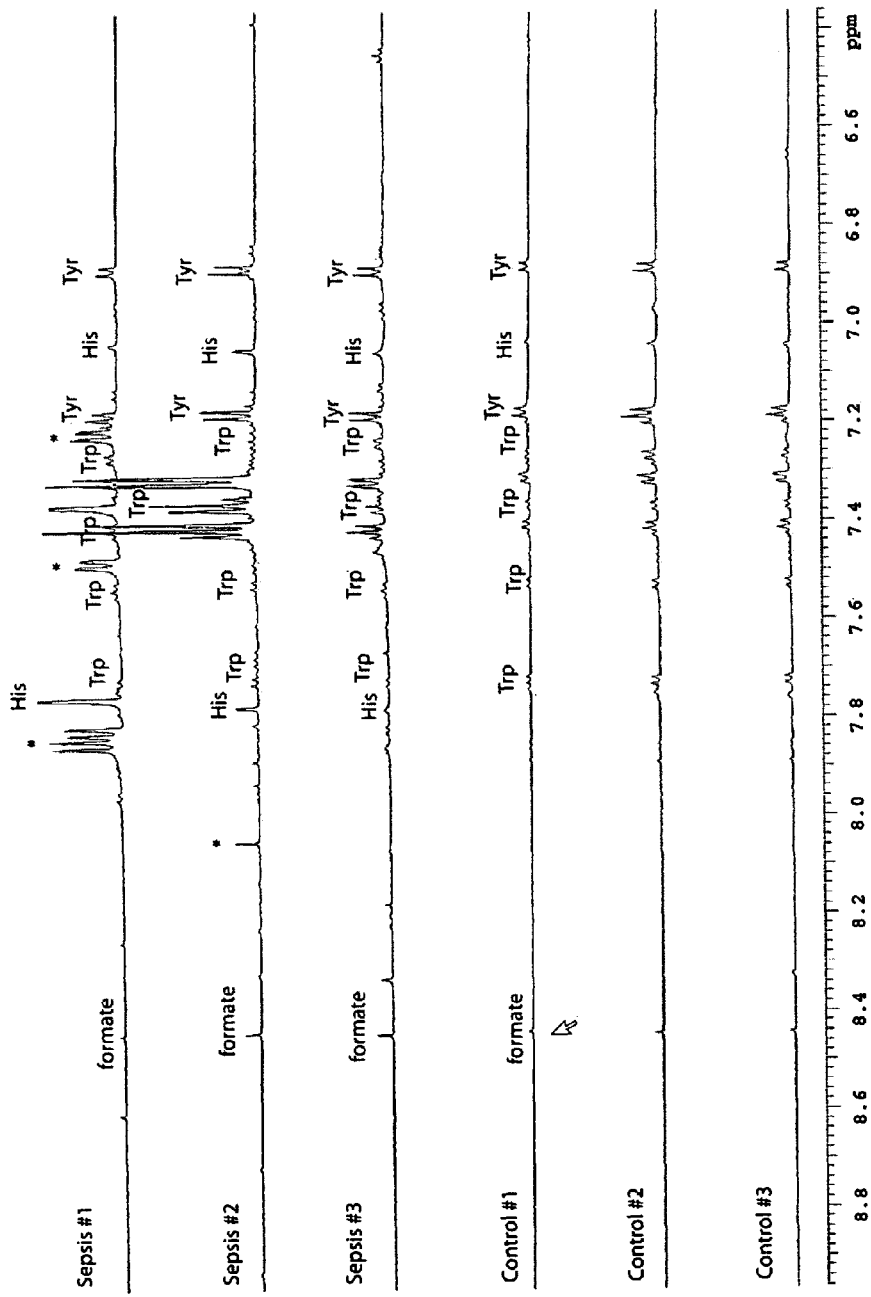
FIG. 20 focuses the NMR traces of FIG. 18 on the aromatic region, revealing excess amounts of aromatic amino acids such as Tyr, Phe, Trp and His.
Figure 21:
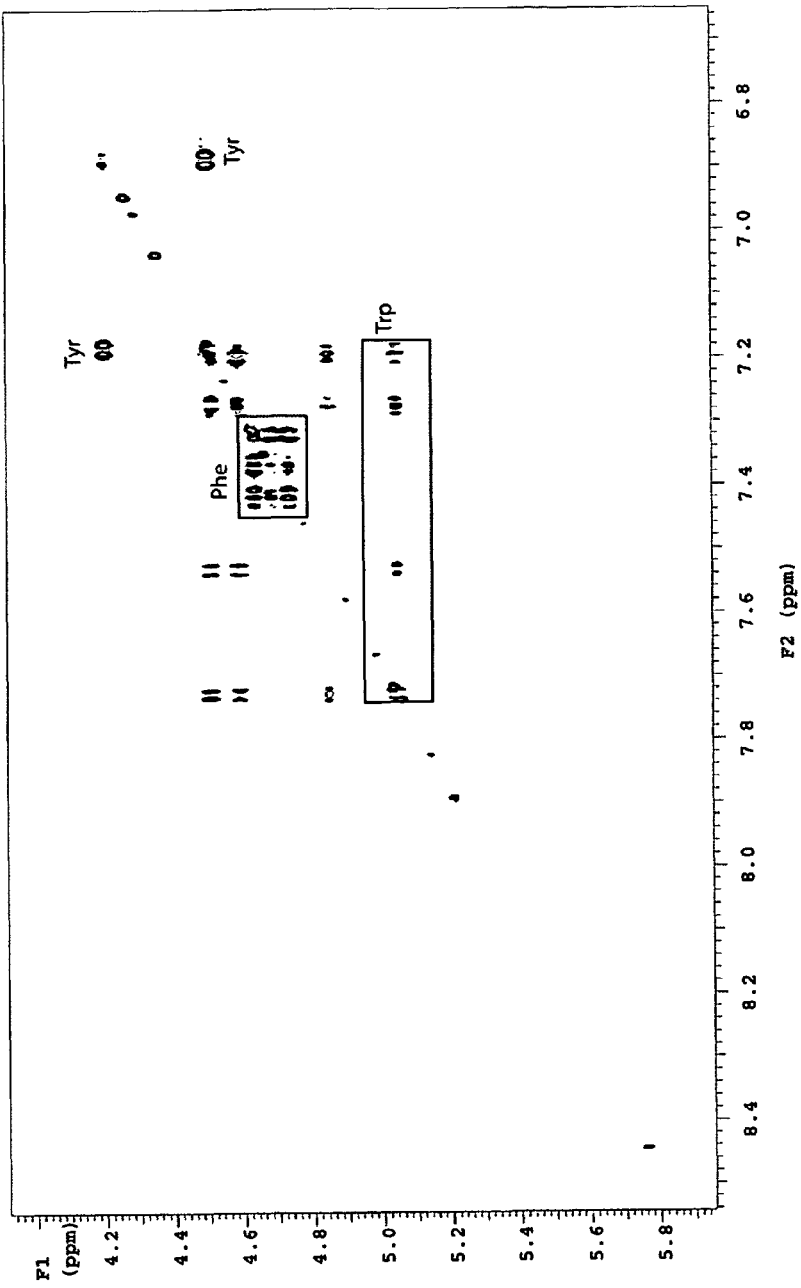
FIG. 21 is a 2D $^1$H-$^1$H TOCSY experiment that assists in metabolite identification.

The human samples are human sera obtained from septic subjects and non-septic subjects ("control"). FIG. 18 demonstrates that large changes in amino acids and other metabolites, consistent with the presented LPS-induced animal models, are observed in humans. The NMR region of the spectrum corresponding to the aliphatic region is presented in FIG. 19. Markers such as citrate (Cit) and lactic acid (Lac) are consistent with the LPS experiments presented herein. There is an about 50% change for some of the amino acids in these septic patients. For example: Ala, Tyr and His ratios increase by >65%, >50%, >50% in sepsis versus control, respectively. Analysis of the aromatic region of the NMR spectra is provided in FIG. 20. Additional markers undergoing change that are not presently identified are labeled with a "*". Such putative markers of interest can be isolated and later identified as known in the art by any of a variety of techniques (e.g., NMR, mass spectrometry, sequencing, etc.). One example of a technique used as part of a metabolite identification process is provided in FIG. 21 (2D 1H-1H TOCSY). The outcome of the biomarker patterns and profile of the detected biomarkers are similar and follow the same trend for the different species examined herein, including birds, rodents and humans. Accordingly, the methods provided herein are compatible with detection and/or diagnosis of disease states for a wide range of species.

REFERENCES

1. Abbott, D. H., et al., *Androgen excess fetal programming of female reproduction: a developmental aetiology for polycystic ovary syndrome?* Hum Reprod Update, 2005. 11(4): p. 357-374.
2. The Rotterdam, E. A.-s.P.c.w.g., *Revised 2003 consensus on diagnostic criteria and long-term health risks related to polycystic ovary syndrome (PCOS).* Hum. Reprod., 2004. 19(1): p. 41-47.
3. Diamanti-Kandarakis, E., et al., *Indices of low-grade chronic inflammation in polycystic ovary syndrome and the beneficial effect of metformin.* Hum. Reprod, 2006. 21(6): p. 1426-1431.
4. Sumner, L. W., P. Mendes, and R. A. Dixon, *Plant metabolomics: large-scale phytochemistry in the functional genomics era.* Phytochemistry, 2003. 62(6): p. 817-36.
5. Rochfort, S., *Metabolomics reviewed: a new "omics" platform technology for systems biology and implications for natural products research.* J Nat Prod, 2005. 68(12): p. 1813-20.
6. Birkemeyer, C., et al., *Metabolome analysis: the potential of in vivo labeling with stable isotopes for metabolite profiling.* Trends Biotechnol, 2005. 23(1): p. 28-33.
7. Weckwerth, W. and O. Fiehn, *Can we discover novel pathways using metabolomic analysis?* Curr Opin Biotechnol, 2002. 13(2): p. 156-60.
8. Dumas, M. E., et al., *Assessment of analytical reproducibility of $^1H$ NMR spectroscopy based metabonomics for large-scale epidemiological research: the INTERMAP Study.* Anal Chem, 2006. 78(7): p. 2199-208.
9. Krishnan, P., N. J. Kruger, and R. G. Ratcliffe, *Metabolite fingerprinting and profiling in plants using NMR.* J Exp Bot, 2005. 56(410): p. 255-65.
10. Weljie, A. M., et al., *Targeted profiling: quantitative analysis of 1H NMR metabolomics data.* Anal Chem, 2006. 78(13): p. 4430-42.
11. Nicholson, J. K., *Global systems biology, personalized medicine and molecular epidemiology.* Mol Syst Biol, 2006.2: p. 52.
12. Shortreed, M. R., et al., *Ionizable Isotopic Labeling Reagent for Relative Quantification of Amine Metabolites by Mass Spectrometry.* Anal. Chem., 2006. 78(18): p. 6398-6403.
13. Romano, R., M. T. Santini, and P. L. Indovina, *A time-domain algorithm for NMR spectral normalization.* J Magn Reson, 2000. 146(1): p. 89-99.
14. Romano, R., et al., *A new algorithm for NMR spectral normalization.* J Magn Reson, 1999. 138(1): p. 115-22.
15. Andersson, F. O., R. Kaiser, and S. P. Jacobsson, *Data preprocessing by wavelets and genetic algorithms for enhanced multivariate analysis of LC peptide mapping.* J Pharm Biomed Anal, 2004. 34(3): p. 531-41.
16. Stoyanova, R., et al., *Automatic alignment of individual peaks in large high-resolution spectral data sets.* J Magn Reson, 2004. 170(2): p. 329-35.
17. Spraul, M., et al., *Automatic reduction of NMR spectroscopic data for statistical and pattern recognition classification of samples.* J Pharm Biomed Anal, 1994. 12(10): p. 1215-25.
18. Wu, W., et al., *Peak alignment of urine NMR spectra using fuzzy warping.* J Chem Inf Model, 2006. 46(2): p. 863-75.
19. Romano, R., et al., *A new time-domain frequency-selective quantification algorithm.* J Magn Reson, 2002. 155(2): p. 226-35.
20. Forshed, J., et al., *A comparison of methods for alignment of NMR peaks in the context of cluster analysis.* J Pharm Biomed Anal, 2005. 38(5): p. 824-32.
21. Prince, J. T. and E. M. Marcotte, *Chromatographic alignment of ESI-LC-MS proteomics data sets by ordered bijective interpolated warping.* Anal Chem, 2006. 78(17): p. 6140-52.
22. Prakash, A., et al., *Signal maps for mass spectrometry-based comparative proteomics.* Mol Cell Proteomics, 2006. 5(3): p. 423-32.
23. Bylund, D., et al., *Chromatographic alignment by warping and dynamic programming as a pre-processing tool for PARAFAC modelling of liquid chromatography-mass spectrometry data.* J Chromatogr A, 2002. 961(2): p. 237-44.
24. Stoyanova, R. and T. R. Brown, *NMR spectral quantitation by principal component analysis. III. A generalized* procedure for determination of lineshape variations. J Magn Reson, 2002. 154(2): p. 163-75.
25. Aranibar, N., et al., *Metabolomic analysis using optimized NMR and statistical methods.* Anal Biochem, 2006. 355(1): p. 62-70.
26. Clote, P. and J. Straubhaar, *Symmetric time warping, Boltzmann pair probabilities and functional genomics.* J Math Biol, 2006. 53(1): p. 135-61.
27. van Nederkassel, A. M., et al., *A comparison of three algorithms for chromatograms alignment.* J Chromatogr A, 2006. 1118(2): p. 199-210.
28. Webb-Robertson, B. J., et al., *A study of spectral integration and normalization in NMR-based metabonomic analyses.* J Pharm Biomed Anal, 2005. 39(3-4): p. 830-6.
29. Fiehn, O., *Metabolomics—the link between genotypes and phenotypes.* Plant Molecular Biology, 2002. 48(1-2): p. 155-171.
30. Voit, E., A. R. Neves, and H. Santos, *The intricate side of systems biology.* Proc Natl Acad Sci USA, 2006. 103(25): p. 9452-7.
31. Mendes, P., D. Camacho, and A. de la Fuente, *Modelling and simulation for metabolomics data analysis.* Biochem Soc Trans, 2005. 33(Pt 6): p. 1427-9.
32. Crampin, E. J., S. Schnell, and P. E. McSharry, *Mathematical and computational techniques to deduce complex biochemical reaction mechanisms.* Prog Biophys Mol Biol, 2004. 86(1): p. 77-112.
33. Antoniotti, M., et al., *Model building and model checking for biochemical processes.* Cell Biochem Biophys, 2003. 38(3): p. 271-86.
34. Price, N. D., J. Schellenberger, and B. O. Palsson, *Uniform sampling of steady-state flux spaces: means to design experiments and to interpret enzymopathies.* Biophys J, 2004. 87(4): p. 2172-86.
35. Kummel, A., S. Panke, and M. Heinemann, *Putative regulatory sites unraveled by network-embedded thermodynamic analysis of metabolome data.* Mol Syst Biol, 2006. 2: p. 2006 0034.
36. Hu, D. and J. M. Yuan, *Time-dependent sensitivity analysis of biological networks: coupled MAPK and PI3K signal transduction pathways.* J Phys Chem A Mol Spectrosc Kinet Environ Gen Theory, 2006. 110(16): p. 5361-70.
37. Schadt, E. E. and P. Y. Lum, *Thematic review series: Systems Biology Approaches to Metabolic and Cardiovascular Disorders. Reverse engineering gene networks to identify key drivers of complex disease phenotypes.* J Lipid Res, 2006. 47(12): p. 2601-13.
38. Hollywood, K., D. R. Brison, and R. Goodacre, *Metabolomics: current technologies and future trends.* Proteomics, 2006. 6(17): p. 4716-23.
39. Purohit, P. V., et al., *Discrimination models using variance-stabilizing transformation of metabolomic NMR data.* Omics, 2004. 8(2): p. 118-30.
40. Franke, L., et al., *Reconstruction of a functional human gene network, with an application for prioritizing positional candidate genes.* Am J Hum Genet, 2006. 78(6): p. 1011-25.
41. Legro, R. S., et al., *Prevalence and Predictors of Risk for Type 2 Diabetes Mellitus and Impaired Glucose Tolerance in Polycystic Ovary Syndrome: A Prospective, Controlled Study in 254 Affected Women.* J Clin Endocrinol Metab, 1999. 84(1): p. 165-169.
42. Anderson, R. N. and B. L. Smith, *Deaths: leading causes for 2001.* Natl. Vital Stat. Rep., 2003. 52: p. 1-85.
43. Pillay, O. C., et al., *The association between polycystic ovaries and endometrial cancer.* Hum. Reprod., 2006. 21(4): p. 924-929.
44. Finley Austin, M. J. and L. Babiss, *Commentary: where and how could biomarkers be used in 2016?* Aaps J, 2006. 8(1): p. E185-9.
45. Hatch, K. A., et al., *Early Detection of Catabolic State via Change in 13C/12C Ratios of Blood Proteins.* BBRC, 1995. 212(3): p. 719.
46. Yang, M., M. W. Pariza, and M. E. Cook, *Dietary conjugated linoleic acid protects against end stage disease of systemic lupus erythematosus in the NZB/W F1 mouse.* Immunopharm. Immunotox., 2000. 22(3): p. 433-49.
47. Porter, W. P., et al., *Identification of disease characteristics using isotope ratios in breath.* Pending, WARF.
48. Porter, W. P., I. W. Treichel, and M. E. Cook, *Passive measurement of isotopes to monitor health.* 1999, WARF: USA.
49. Eghbalnia, H. R., et al., *High-resolution iterative frequency identification for NMR as a general strategy for multidimensional data collection.* J Am Chem Soc, 2005. 127(36): p. 12528-36.
50. Eghbalnia, H. R., et al., *Probabilistic Identification of Spin Systems and their Assignments including Coil-Helix Inference as Output (PISTACHIO).* J Biomol NMR, 2005. 32(3): p. 219-33.
51. Eghbalnia, H. R., et al., *Protein energetic conformational analysis from NMR chemical shifts (PECAN) and its use in determining secondary structural elements.* J Biomol NMR, 2005. 32(1): p. 71-81.
52. Xu, H., et al., *Chronic inflammation in fat plays a crucial role in the development of obesity-related insulin resistance.* J. Clin. Invest., 2003. 112(12): p. 1821-1830.
53. Sjøholm, Å. and T. Nyström, *Inflammation and the etiology of type 2 diabetes.* Diab./Metab. Res. Rev., 2006. 22(1): p. 4-10.
54. Diamanti-Kandarakis, E., et al., *Inflammatory and endothelial markers in women with polycystic ovary syndrome.* Eur J Clin Invest, 2006. 36(10): p. 691-697.
55. Hotamisligil, G. S., N. S. Shargill, and B. M. Spiegelman, *Adipose expression of tumor necrosis factor-alpha: direct role in obesity-linked insulin resistance.* Science, 1993. 259(5091): p. 87-91.
56. Pickup, J. C. and M. A. Crook, *Is Type II diabetes mellitus a disease of the innate immune system?* Diabetologia, 1998. 41(10): p. 1241.
57. Fleming, R., *The use of insulin sensitising agents in ovulation induction in women with Polycystic Ovary Syndrome.* Hormones, 2006. 5(3): p. 171-178.
58. Ferraz, T. P. L., et al., *Comparison of six methods for the extraction of lipids from serum in terms of effectiveness and protein preservation.* J Biochem Biophys Meth, 2004. 58(3): p. 187.
59. Li, Z. and C. Chan, *Inferring pathways and networks with a Bayesian framework.* Faseb J, 2004. 18(6): p. 746-8.

TABLE 1

NMR-Data Entry for chicken and mice biometabolites (plotted in FIG. 13)

| Chicken | | formate | 3OHB-1 | 3OHB-2 | Acetoacetate | lactateCH3 | lactateCH |
|---|---|---|---|---|---|---|---|
| weight | 4 hour–> | −1 | 1 | 2 | 1 | −1 | −1 |
| 381 | | 0 | 1 | 1 | 1 | 1 | 1 |
| 382 | | −1 | 0 | 0 | 1 | −1 | −1 |
| 384 | | −1 | 1 | 1 | 1 | 1 | 0 |
| 385 | | −1 | 1 | 1 | 1 | −1 | −1 |
| 386 | | 1 | 1 | 1 | 1 | 2 | 1 |
| 387 | | −1 | 1 | 1 | 1 | −1 | 0 |
| 388 | | | | | | | |
| 381 | 8 hour–> | −1 | −1 | 1 | −1 | −1 | −1 |
| 382 | | −1 | −1 | −1 | −1 | −1 | −1 |
| 384 | | −1 | −1 | −1 | −1 | −1 | −1 |
| 385 | | −1 | −1 | 1 | −1 | −1 | −1 |
| 386 | | −1 | −1 | 0 | −1 | −1 | −1 |
| 387 | | −1 | −1 | −1 | −1 | −1 | −1 |
| 388 | | −1 | 1 | 2 | −1 | −1 | −1 |

| Chicken | | Glucose-Ca | GlucoseCB | Ala-CH3 | Lys-1 | aaCH3 |
|---|---|---|---|---|---|---|
| weight | 4 hour–> | 1 | 1 | −1 | 1 | 1 |
| 381 | | 1 | 1 | 1 | 1 | 1 |
| 382 | | 1 | 1 | −1 | 1 | 1 |
| 384 | | 1 | 1 | −1 | 1 | 1 |
| 385 | | 0 | 0 | −1 | 1 | 1 |
| 386 | | 1 | 1 | 2 | 1 | 1 |
| 387 | | 1 | 1 | −1 | 1 | 1 |
| 388 | | | | | | |
| 381 | 8 hour–> | 1 | 1 | −1 | 1 | 0 |
| 382 | | 1 | 0 | −1 | −1 | 0 |
| 384 | | 1 | 1 | −1 | 1 | 0 |
| 385 | | 1 | 1 | −1 | 0 | 0 |
| 386 | | 1 | 1 | −1 | 0 | 0 |
| 387 | | 1 | 1 | −1 | −1 | 0 |
| 388 | | 1 | 1 | −1 | 1 | 0 |

| Mice | | formate | 3OHB-1* | 3OHB-2* | Acetoacetate | lactateCH3 | lactateCH |
|---|---|---|---|---|---|---|---|
| Weight | 4-24 hrs | | | | | | |
| Saline 1 | | 0 | 0 | 0 | −1 | 0 | 0 |
| Saline 2 | | 0 | 0 | 0 | 0 | 0 | 0 |
| Saline 3 | | 0 | 0 | 0 | −1 | 0 | 0 |
| LPS1 | 4 hour–> | 1 | 1 | 1 | 0 | 1 | 1 |
| LPs2 | | 1 | 1 | 1 | 1 | 1 | 1 |
| LPS3 | | −1 | 1 | 1 | −1 | −1 | −1 |
| LPs4 | | −1 | 0 | 1 | −1 | −1 | −1 |
| LPS5 | | −1 | 1 | 1 | −1 | −1 | −1 |
| LPS6 | | 0 | 1 | 1 | 1 | −1 | −1 |
| LPS1 | 8 hour–> | −1 | 1 | 1 | −1 | −1 | −1 |
| LPs2 | | −1 | 1 | 1 | −1 | −1 | −1 |
| LPS3 | | −1 | 1 | 1 | −1 | 1 | 1 |
| LPs4 | | −1 | 1 | 1 | −1 | −1 | −1 |
| LPS5 | | 0 | −1 | −1 | 1 | 1 | 1 |
| LPS6 | | −1 | 1 | 0 | 1 | 1 | 1 |
| LPS1 | 24 hour–> | 0 | 1 | | 0 | 0 | 0 |
| LPs2 | | −1 | 0 | | 0 | 0 | 0 |
| LPS3 | | 0 | 0 | | 0 | 0 | 0 |
| LPs4 | | 0 | 0 | | −1 | 0 | 0 |
| LPS5 | | 0 | 0 | | 0 | 0 | 0 |
| LPS6 | | 0 | 0 | | −1 | 0 | 0 |

| Mice | | Glucose-Ca | GlucoseCB | Ala-CH3 | Lys-1 | aaCH3 |
|---|---|---|---|---|---|---|
| Weight | 4-24 hrs | | | | | |
| Saline 1 | | 0 | 0 | −1 | 0 | |
| Saline 2 | | 0 | 0 | 0 | 0 | |
| Saline 3 | | 0 | 0 | 0 | 0 | |
| LPS1 | 4 hour–> | −1 | −1 | −1 | 0 | 0 |
| LPs2 | | −1 | −1 | −1 | 0 | 0 |
| LPS3 | | −1 | −1 | −1 | 0 | 0 |
| LPs4 | | −1 | −1 | −1 | 0 | 0 |
| LPS5 | | −1 | −1 | −1 | 0 | 0 |
| LPS6 | | −1 | −1 | −1 | 0 | 0 |
| LPS1 | 8 hour–> | −1 | −1 | 0 | 0 | 0 |
| LPs2 | | −1 | −1 | −1 | 0 | 0 |
| LPS3 | | −1 | −1 | 0 | 0 | 0 |
| LPs4 | | −1 | −1 | −1 | 0 | 0 |
| LPS5 | | 1 | 1 | 1 | 0 | 0 |

TABLE 1-continued

NMR-Data Entry for chicken and mice biometabolites (plotted in FIG. 13)

| | | | | | | |
|---|---|---|---|---|---|---|
| LPS6 | | 0 | 0 | 1 | 0 | 0 |
| LPS1 | 24 hour-> | 0 | 0 | 0 | 0 | 0 |
| LPs2 | | 0 | 0 | 0 | 0 | 0 |
| LPS3 | | 0 | 0 | 0 | 0 | 0 |
| LPs4 | | 0 | 0 | 0 | 0 | 0 |
| LPS5 | | 0 | 0 | 0 | 0 | 0 |
| LPS6 | | 0 | 0 | 0 | 0 | 0 |

TABLE 2

NMR-Data Entry for mice biometabolites

| Mice | | formate | 3OHB-1* | 3OHB-2* | Acetoacetate | lactateCH3 | lactateCH |
|---|---|---|---|---|---|---|---|
| Weight | 4-24 hrs | | | | | | |
| Saline 1 | | same | same | same | down | same | same |
| Saline 2 | | same | same | same | same | same | same |
| Saline 3 | | same | same | same | down | same | same |
| New 1-2 hrs | | | | | | | |
| saline 1 | 0 hr-> | 0 | N/A | N/A | 0 | 0 | 0 |
| m2 | | 0 | N/A | N/A | 0 | 0 | 0 |
| m3 | | 0 | N/A | N/A | 0 | 0 | 0 |
| Saline 1 | 1 hr-> | 0.5 | N/A | N/A | 0 | 1 | 1 |
| m2 | | 2 | N/A | N/A | 2 | 0 | 0 |
| m3 | | 3 | N/A | N/A | 1 | 0 | 0 |
| Saline 1 | 2 hrs-> | 0 | N/A | N/A | 2 | 2 | 2 |
| m2 | | −1 | N/A | N/A | −1 | 1 | 1 |
| m3 | | −1 | N/A | N/A | 1.5 | 2 | 2 |
| LPS1 | 4 hour-> | up | up | up | slightly down | up | up |
| LPs2 | | up | up | up | up | up | up |
| LPS3 | | down | up | up | down | down | down |
| LPs4 | | down | same | up | down | down | down |
| LPS5 | | down | high | high | down | down | down |
| LPS6 | | same | up | up | up | down | down |
| LPS1 | 8 hour-> | down | high | high | down | down | down |
| LPs2 | | down | high | high | down | down | down |
| LPS3 | | down | high | high | down | up | up |
| LPs4 | | down | med high | med high | down | down | down |
| LPS5 | | same | down | down | up | up | up |
| LPS6 | | down | med high | same | up | up | up |
| LPS1 | 24 hour-> | same | high | | same | same | same |
| LPs2 | | down | same | | same | same | same |
| LPS3 | | same | same | | same | same | same |
| LPs4 | | same | same | | down | same | same |
| LPS5 | | same | same | | same | same | same |
| LPS6 | | same | same | | down | same | same |

| Mice | | Glucose-Ca | GlucoseCB | Ala-CH3 | Lys-1 | |
|---|---|---|---|---|---|---|
| Weight | 4-24 hrs | | | | | aaCH3 |
| Saline 1 | | same | same | slightly down | same | |
| Saline 2 | | same | same | slightly up | same | |
| Saline 3 | | same | same | slightly up | same | |
| New 1-2 hrs | | | | | | |
| | | | | | | Citrate |
| saline 1 | 0 hr-> | 0 | 0 | 0 | | 0 |
| m2 | | 0 | 0 | 0 | | 0 |
| m3 | | 0 | 0 | 0 | | 0 |
| | | | | | | citrate |
| Saline 1 | 1 hr-> | 0 | 0 | 0 | | 1 |
| m2 | | 1 | 1 | 1 | | 1 |
| m3 | | 1 | 1 | 1 | | −1 |
| | | | | | | 0 |
| Saline 1 | 2 hrs-> | 1 | 1 | 2 | | −1 |
| m2 | | 2 | 2 | 2 | | 1 |
| m3 | | 0 | 0 | 1 | | |
| | | | | | | aaCH3 |
| LPS1 | 4 hour-> | down | down | down | missing data | complex does not change |
| LPs2 | | down | down | down | | |
| LPS3 | | down | down | down | | |
| LPs4 | | down | down | down | | |
| LPS5 | | down | down | down | | |

TABLE 2-continued

| | NMR-Data Entry for mice biometabolites | | | |
|---|---|---|---|---|
| LPS6 | | down | down | down |
| LPS1 | 8 hour–> | down | down | same |
| LPs2 | | down | down | down |
| LPS3 | | down | down | slightly up |
| LPs4 | | down | down | down |
| LPS5 | | up | up | high |
| LPS6 | | same | same | high |
| LPS1 | 24 hour–> | same | same | same |
| LPs2 | | same | same | same |
| LPS3 | | same | same | same |
| LPs4 | | same | same | same |
| LPS5 | | slightly up | same | same |
| LPS6 | | same | same | same |

We claim:

1. A method for providing information useful for diagnosing a disease state in a subject comprising:
   a) obtaining a biological sample comprising a plurality of biomarkers from the subject, wherein the biomarker levels are related to the disease state, and the disease state is sepsis;
   b) detecting the plurality of biomarkers;
   c) determining a profile of the detected biomarkers; and
   d) comparing the profile of the detected biomarkers to a standard biomarker profile, wherein the profile of the detected biomarkers comprise Ala, Tyr and His each having increased levels of at least 50% compared to the standard biomarker profile, thereby providing information useful for diagnosing sepsis.

2. The method of claim 1, wherein the biological sample comprises blood or blood plasma.

3. The method of claim 1, wherein the standard biomarker level is from an internal reference.

4. The method of claim 1, wherein a sample metabolome portrait is determined from the biomarker profile and the information useful for diagnosing the disease state is obtained by fitting the sample metabolome portrait to a standard metabolome phase portrait.

5. The method of claim 1 further comprising:
   a) repeating the steps of claim 1 on a second biological sample, wherein the second biological sample is obtained from the subject at a different time; and
   b) comparing the biomarker profiles of the two biological samples to provide information useful for diagnosing the disease state.

6. The method of claim 1 wherein the biomarkers are detected by NMR, mass spectroscopy, ELISA, fluorescence labeling techniques, flow cytometry, chromatography, capillary electrophoresis or chemical sensor.

7. The method of claim 1, wherein the disease state is associated with a viral infection or a bacterial infection.

8. The method of claim 1, wherein the subject is a mammal and said mammal is selected from the group consisting of avian, bovine, swine, horse, sheep and human.

9. The method of claim 1, wherein the plurality of biomarkers form a clique capable of providing information useful for diagnosing the disease state.

* * * * *